US008603123B2

(12) United States Patent
Todd

(10) Patent No.: US 8,603,123 B2
(45) Date of Patent: Dec. 10, 2013

(54) BENIGN PROSTATIC HYPERPLASIA SURGICAL SYSTEM FEATURING MECHANICAL CORING PROBE WITH LIVE ASPIRATION

(75) Inventor: Michael Edward Todd, Simi Valley, CA (US)

(73) Assignee: UroTech, Inc., Simi Valley, CA (US)

( * ) Notice: Subject to any disclaimer, the term of this patent is extended or adjusted under 35 U.S.C. 154(b) by 583 days.

(21) Appl. No.: 12/430,532

(22) Filed: Apr. 27, 2009

(65) Prior Publication Data

US 2009/0270791 A1    Oct. 29, 2009

Related U.S. Application Data

(60) Provisional application No. 61/048,427, filed on Apr. 28, 2008, provisional application No. 61/104,382, filed on Oct. 10, 2008, provisional application No. 61/120,115, filed on Dec. 5, 2008, provisional application No. 61/086,775, filed on Aug. 6, 2008.

(51) Int. Cl.
*A61B 17/32* (2006.01)

(52) U.S. Cl.
USPC .......................................... 606/167; 606/170

(58) Field of Classification Search
USPC ............. 606/159, 169, 170, 171, 180, 79–85, 606/172, 173, 174
See application file for complete search history.

(56) References Cited

U.S. PATENT DOCUMENTS

| 4,762,128 A | 8/1988 | Rosenbluth |
| 4,932,956 A | 6/1990 | Reddy et al. |
| 4,973,321 A * | 11/1990 | Michelson .................... 604/523 |
| 5,019,089 A | 5/1991 | Farr |
| 5,163,952 A | 11/1992 | Froix |
| 5,234,456 A | 8/1993 | Silvestrini |
| 5,370,677 A | 12/1994 | Rudie et al. |
| 5,403,277 A * | 4/1995 | Dodge et al. .................... 604/30 |
| 5,571,130 A | 11/1996 | Simpson et al. |
| 5,575,811 A | 11/1996 | Reid et al. |
| 5,643,304 A | 7/1997 | Schechter et al. |
| 5,651,783 A * | 7/1997 | Reynard ............................ 606/4 |
| 6,007,556 A * | 12/1999 | Kablik et al. ................. 606/180 |
| 6,053,923 A * | 4/2000 | Veca et al. ...................... 606/80 |
| 6,156,049 A | 12/2000 | Lovato et al. |
| 6,251,121 B1 * | 6/2001 | Saadat .......................... 606/180 |
| 6,289,249 B1 | 9/2001 | Arndt et al. |
| 6,424,869 B1 | 7/2002 | Carr et al. |
| 6,477,426 B1 | 11/2002 | Fenn et al. |

(Continued)

*Primary Examiner* — Thomas McEvoy
(74) *Attorney, Agent, or Firm* — SoCal IP Law Group LLP; Guy L. Cumberbatch; Steven C. Sereboff

(57) ABSTRACT

The invention comprises an atherectomy probe for mechanically cutting core prostatic tissue to alleviate the condition of benign prostatic hyperplasia (BPH) or for use in orthopedic procedures. The blade shapes and lengths are adaptable but in a preferred embodiment the device includes an end-cutting bur tip. The cutting motion may be one of: guillotine (incising between two parallel edges), radial reciprocating (changing radial directions and cuts between two horizontal edges), circular (continuously radial in one direction), and end-cutting, etc. The power source used to drive the blade may be one of: pneumatic, hydraulic, manual mechanical, electrical, solar, etc. The probe also includes several channels that may be used for providing live aspiration and removal of severed tissue and fluids, as well as insufflation of gases and optionally, pharmaceuticals and/or a secondary therapy. The instrument is designed for use in open, endoscopic, and minimally invasive transurethral or transperineal surgical procedures.

7 Claims, 16 Drawing Sheets

(56) References Cited

U.S. PATENT DOCUMENTS

| | | |
|---|---|---|
| 6,491,672 B2 | 12/2002 | Slepian et al. |
| 6,902,542 B2 | 6/2005 | Gordon |
| 6,986,764 B2 | 1/2006 | Davenport et al. |
| 6,989,400 B2 | 1/2006 | Tidmarsh |
| 2001/0047147 A1 | 11/2001 | Slepian et al. |
| 2002/0007190 A1 | 1/2002 | Wulfman et al. |
| 2004/0153111 A1* | 8/2004 | Hosoada ................ 606/167 |
| 2006/0041268 A1* | 2/2006 | Shores et al. ............ 606/180 |
| 2007/0010823 A1* | 1/2007 | Kucklick ................. 606/80 |
| 2008/0015621 A1 | 1/2008 | Emanuel |
| 2008/0103412 A1 | 5/2008 | Chin |
| 2008/0125772 A1 | 5/2008 | Stone et al. |
| 2008/0188811 A1 | 8/2008 | Kim |
| 2009/0060977 A1 | 3/2009 | Lamson et al. |

* cited by examiner

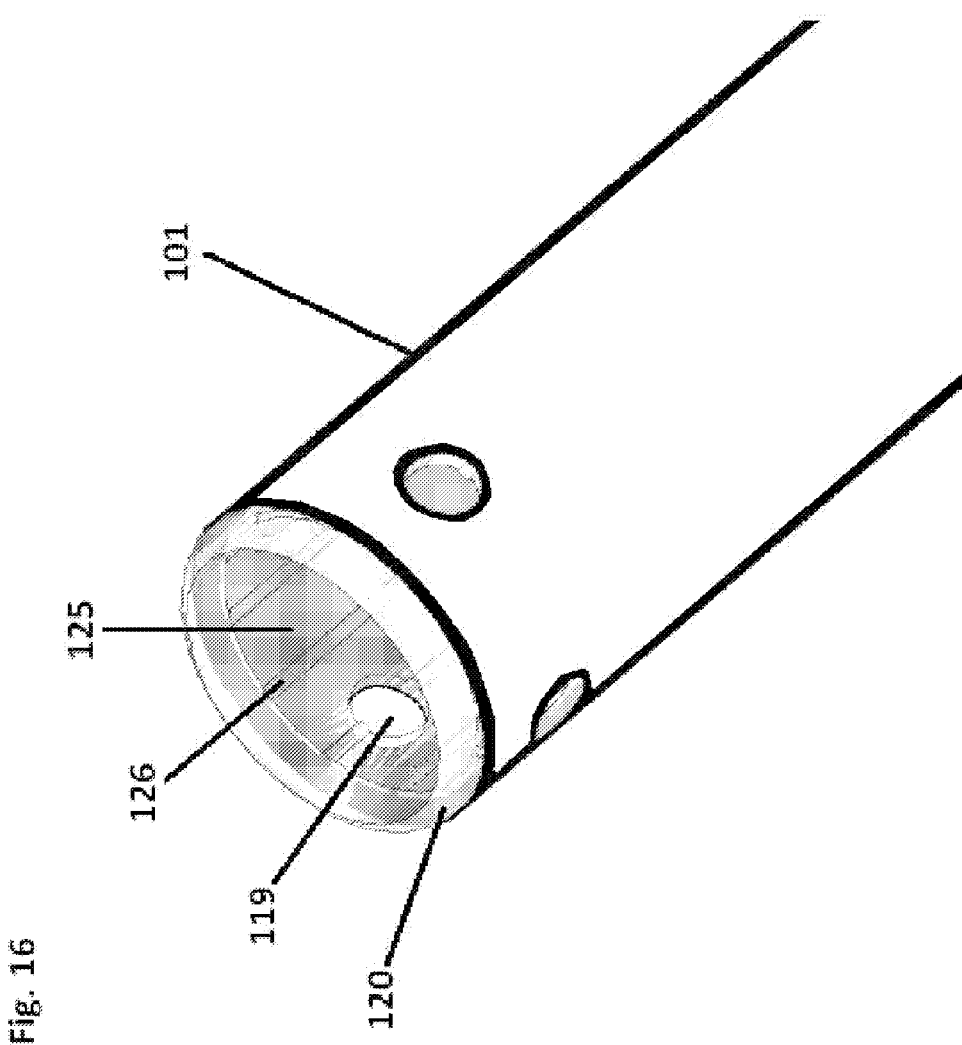

BENIGN PROSTATIC HYPERPLASIA SURGICAL SYSTEM FEATURING MECHANICAL CORING PROBE WITH LIVE ASPIRATION

BACKGROUND OF THE INVENTION

1. Field of the Invention

The invention relates to the art of medical devices, systems, and methods for cutting and removing tissue with the option of also providing auxiliary functions through the same instrument. More specifically, the invention is designed to mechanically core prostate tissue via a transperineal minimally invasive surgery. The invention is directed at alleviating the condition of benign prostatic hyperplasia (BPH) characterized by generally non-malignant (benign) proliferation of the cells making up the prostate gland in males.

2. Description of the Related Art

The prostate is a walnut-sized gland located beneath the bladder and in front of the rectum. The urethra passes through the prostate to the bladder neck. Commonly, as a man ages, the prostate begins to grow and this growth often results in the prostate squeezing the urethra within it. This proliferation of tissue in the prostate gland is known as benign prostatic hyperplasia (BPH). BPH causes urination problems when an enlarged prostate presses against the urethra narrowing the canal. BPH is estimated to affect over fifty percent of men over the age of sixty.

Approximately one-third of prostate tissue is anterior to the urethra and consists of fibromuscular tissue physiologically related to the urethra and bladder. Approximately two-thirds of prostate tissue is posterior to the urethra and consists of glandular tissue. BPH involves bilateral nodular expansion of prostate tissue in a transition zone between the fibromuscular tissue and the glandular tissue. Without treatment, BPH obstructs the urethra to cause a slow or interrupted urinary stream, nocturia, increased frequency of urination, a sense of urinary urgency, and incontinence. Occasionally, BPH is also responsible for more severe problems including uraemia, hydronephrosis, and urinary tract infections. Uraemia is retention in the bloodstream of waste products normally excreted in the urine. Hydronephrosis is the dilation of the branches of the pelvic cavity and the kidney, caused by an accumulation of urine resulting from obstruction of normal outflow.

Systems and methods exist to treat BPH. These include drug therapy, non-surgical procedures, and surgical procedures (i.e. prostatectomy).

Drugs often have side effects and must be taken long-term for continued effectiveness. For an example of pharmaceutical treatment of BPH, see U.S. Pat. No. 6,989,400 ("Treatment of benign prostatic hyperplasia" by George Tidmarsh) assigned to Threshold Pharmaceuticals, Inc. disclosing the administration of lonidamine.

Non-surgical (without mechanical cutting) conventional BPH procedures, such as thermotherapy, use various forms of energy (radiofrequency, microwave, ultrasound, etc.) to ablate the prostate tissue. The application of energy is usually overbroad and results in ablation-induced collateral damage and necrosis (cell death) of healthy urethral tissue. These non-mechanical energy delivery devices alleviate symptomatic pressure and widen the constricted urethra by coring out a new urethral channel formed by scar tissue. However, overly aggressive scar tissue proliferation occasionally results in some individuals, and can have side effects including seminal vesicle blockage (leading to reverse ejaculation, dry climax, etc.) and an increase in volume that creates pressure and undermines the achievement of volume reduction in the prostate. Other technologies such as TURP (TransUrethral Resection of the Prostate) and LASER (Light Amplification by Stimulated Emission of Radiation) also destroy healthy tissue including important muscles at the bladder neck. The bladder neck is a common target for treatment. The widening with both TURP and LASER damage the bladder's muscular structure that can lead to bladder incontenence and can also reduce or eliminate the bladder neck's ability to constrict upon sexual stimulation/ejaculation allowing the ejaculate to travel in reverse into the male's bladder, thus yielding him with reverse ejaculation.

For example, U.S. Pat. No. 6,289,249 ("Transcatheter microwave antenna" by Arndt et al.) assigned to the U.S. Government as represented by NASA describes a system comprising a catheter with a small diameter, disk loaded, monopole antenna surrounded by fusion material. Microwaves from the antenna heat prostatic tissue to promote necrosing. The fusion material absorbs energy to keep the urethra cool. The pressure of the prostatic tissue against the urethra is relieved as the body reabsorbs the necrosed or dead tissue. (For reference to reabsorption by the body see Abstract, 13:7 and 15:42.) Resorption of tissue in transurethral prostate treatments is also referred to in U.S. Published Application No. Pub. App.) 20080125772 ("Tuned RF energy and electrical tissue characterization for selective treatment of target tissues" by Corbett W. Stone, et al.) assigned to Minnow Medical, Inc (San Diego, Calif.) at paragraph [0095]. Relying on the body to reabsorb or otherwise dispose of severed, damaged and/or dead tissue is risky and inconsistent as all patients heal differently. The time in which the patients can expect to experience relief from the procedure may take several weeks to realize, if at all. Other potential challenges are that the tissue can fail to disintegrate properly and can be transported to other regions of the body to cause complications there from blockage (i.e. thrombosis, lumen occlusion, obstruction at junctions to interfere with natural drainage, pressure accumulation etc.). The TransUrethral Core Prostectomy (TUCP™) & Trans-Perineal Core Prostatectomy (TPCP™) devices and methods of the present invention provide for immediate removal of bulk core prostatic tissue to provide instantaneous relief of BPH. Our technology also allows core bulk tissue removal at the bladder neck while our system does not target or damage the bladder neck's muscular structure. This will reduce or eliminate reverse ejaculation when used as indicated.

Other drawbacks of microwave thermal therapy systems are addressed in U.S. Pat. No. 5,370,677 ("Gamma matched, helical dipole microwave antenna with tubular-shaped capacitor" by Rudie, et al.) assigned to Urologix, Inc. These include overbroad generation of heat that necroses healthy tissue also and unpredictable heating patterns and radiation lengths that are not easily adjusted (1:65-3:3). U.S. Pat. No. '677 also refers to necrosed tissue being "resorbed by the body" rather than removed (2:11-14). The only reference to removal is locally removing tissue by heating and necrosing rather than externally removing the necrosed tissue from the body (4:24-27).

U.S. Pat. No. 5,575,811 ("Benign prostatic hyperplasia treatment catheter with urethral cooling" by Reid, et al.) assigned to Urologix, Inc. discloses a similar system to that of the '249 patent in which a catheter having an antenna is used to heat tissue. U.S. Pat. No. '811 also discloses a "coolant fluid" to be circulated in a chamber between the catheter shaft and urethral wall to keep cool the body lumen. The TUCP™ and TPCP™ system of the present invention is distinguishable from the Urologix, Inc. '811 patent because it does not require a catheter and it does not use heat to destroy the urethral lining or excess prostate tissue. In the present invention if a coolant fluid is used it is within a balloon rather than a catheter chamber. The present invention is more efficient because it uses a device to precisely cut and remove bulk core prostatic tissue via mechanical coring rather than heat to destroy tissue. Therefore the coolant does not interfere with tissue destruction by coring whereas a coolant would work against and be counter-productive to heating.

Another non-surgical approach for ameliorating the symptoms of BPH without removing the problem at its source is a urethral stent. U.S. Pat. No. 4,762,128 ("Method and apparatus for treating hypertrophy of the prostate gland" by Robert Rosenbluth) assigned to Advanced Surgical Intervention, Inc. discloses an expandable tubular stent to be used with an expansion catheter and left in place for long-term patency of the urethral lumen. Other stents are disclosed in U.S. Pat. No. 5,234,456 ("Hydrophilic stent" by Thomas Silverstrini) assigned to Pfizer Hospital Products Group, Inc. and U.S. Pat. No. 5,163,952 ("Expandable polymeric stent with memory and delivery apparatus and method" by Michael Froix and unassigned).

U.S. Pat. No. 4,932,956 by Reddy et al. and assigned to American Medical Systems, Inc. discloses a "Prostate balloon dilator". The balloon dilator is part of a catheter and urine is drained through the catheter (6:16-17 and claim 7). The apparatus of U.S. Pat. No. '956 simply dilates the urethral lumen and is then removed without damaging any urethral tissue. The present invention has the objective of actually targeting and removing excessive amounts of core prostatic tissue via TransPerineal Core Prostatectomy (TPCP™) and/or TransUrethral Core Prostectomy (TUCP™). Preferably, the mechanical coring probe of the present invention may be inserted transperineally or transurethrally with or without the assistance of the transurethral protective delivery sheaths and access systems as are respectively disclosed in commonly owned co-pending application Ser. No. 61/048,427 and Ser. No. 61/086,775. To the extent that they are not inconsistent with the present application, Application Ser. No. 61/048,427 and Ser. No. 61/086,775 are incorporated by reference. Unlike the protective delivery sheaths disclosed in these applications for use with the probe disclosed herein, the balloon in U.S. Pat. No. '956 is not used as a sheath for instrument delivery and retrieval, for urethral protection against irritation, and/or for urine drainage (rather, urine is drained through the catheter). The present invention can be used with dilators to create the working space. However, this is not always essential and these dilators need not be balloon dilators but can include other means such as dilating trocars with progressively increasing diameters.

Conventional surgical systems for removal of the prostate (prostatectomy) are bulky and expensive and their use generally results in the loss of fertility. Prostatectomy is typically performed as an in-patient procedure requiring general anesthesia, a longer term hospital stay, and a significant recovery time before a patient returns to work.

The current gold standard therapeutic approaches include transurethral resection of the prostate (TURP) and laser surgery. For example, U.S. Pat. No. 6,156,049 ("Method and apparatus for transurethral resection of the prostate" by Lovato, et al.) assigned to Coherent Inc. discloses a TURP procedure and U.S. Pat. No. 6,986,764 ("Method and system for photoselective vaporization of the prostate, and other tissue" by Davenport, et al.) assigned to Laserscope discloses a laser surgery procedure. Both the TURP and LASER technologies destroy the urethral lining, prostatic capsule, and bladder neck's muscular structure as well as any other soft tissue with which they engage. TURP and LASER both have significant side effects, such as reverse ejaculation and pain/discomfort upon urination, as a result of built-up scar tissue and damage to the bladder neck's musculature. The present invention is minimally invasive and preserves the urethral lining and prostatic capsule by, at most, only making a very small self-sealing "micro puncture" in the urethral lining when applying the technology in the TUCP™. When using the TPCP™ technology, a self-sealing micro puncture is only created to the prostatic capsule and the urethral lining is left pristine for reduced pain, discomfort, and normal urinal flow patterns post the core bulk tissue removal procedure. The micro puncture of the prostatic capsule is unique to access the core of the prostatic lobes with the atherectomy system but also to control bleeding by maintaining an enclosed environment which will self-seal if the micro puncture is maintained during the procedure. The probe is delivered directly to the target area of the bulk core prostatic tissue that is to be removed to alleviate the symptoms of BPH.

There are minimal reference art patents covering surgical approaches to BPH that rely on transurethral mechanical coring atherectomy probes and even less that apply to transperineal access procedures. Atherectomy generally refers to the mechanical removal of material from a body lumen by a rotating, reciprocating, end cutting, or guillotine cutting device typically inserted through a catheter that then aspirates out the separated tissue. Only two patents were found referring to "benign prostatic hyperplasia" in the "Abstract" and to "transurethral" in a claim and both of these (U.S. Pat. No. 6,477,426 and U.S. Pat. No. 6,424,869) use heating/microwave methods rather than mechanical cutting (searches performed on Mar. 12, 2008, same results on Sep. 17, 2008). In the context of the present application and invention mechanical cutting is used to refer to cutting via a structurally sharp blade rather than, for example, severing or resecting tissue with current in cauterizing or electrosurgical electrodes. Only one other U.S. patent was found to contain the term combination "atherectomy probe" (search performed on Sep. 9, 2008). U.S. Pat. No. 5,019,089 ("Atherectomy advancing probe and method of use" by Andrew F. Farr) assigned to Interventional Technologies Inc. (San Diego, Calif.) is primarily concerned with removing obstructive tissue and plaque from the lumens of arteries to restore blood flow. There is no mention of application to the prostate's core transurethrally or transperineally through a micro puncture of the urethral wall and/or a micro puncture of the prostatic capsule. The objective is incremental advancement (including use of advancement tape) rather than cutting and removal mechanisms. A rotating cutter is disclosed but there is no disclosure of the following cutting mechanisms: radial reciprocating, guillotine and end-cutting. Although a suction system for tissue removal during the procedure and a port for injecting medicinal fluids are briefly disclosed, there is no enablement as to potential or optimal designs or how these would operate in conjunction with the rotating cutter (3:38-42, 8:10-18).

U.S. Pub. App. 20080125772 of Stone, et al. (fully cited above) also teaches the combination of more than one therapy (i.e. drugs, medicinal fluids, or radiation) in a single device (see paragraphs [0098], [0099], [0118], and [0138]). However, the published application does not teach mechanical cutting/coring with a sharp blade and thus does not include this component in any of the combinations. Rather, U.S. Pub. App. '772 emphasizes electrosurgical energy delivery by electrodes (see Abstract, claims 9, 11, 18, 26, 33, etc.). Further, the publication teaches using the different features or therapies sequentially while in the present invention they could be administered simultaneously. In fact, in the present invention it is expected that suction removal will be performed simultaneously with coring to provide a continuous process that does not provide severed tissue with the opportunity to migrate before external removal.

U.S. Pat. No. 5,571,130 ("Atherectomy and prostectomy system") by John B. Simpson, et al. assigned to Advanced Cardiovascular Systems, Inc. (Santa Clara, Calif.), unlike U.S. Pat. No. '089 above and as its title implies, specifically refers to use of the cutting tool on prostate tissue and not just for relieving blockages in the arteries. Like the present invention, U.S. Pat. No. '130 is directed to "precisely deliver a sharp cutting action to the diseased portion of . . . the gland with optimal efficiency" (2:38-40). However, the present invention teaches a device with a greater variety of: (i) cutting mechanisms including several different range of motion (ROM) patterns, (ii) power sources for activation, and (iii) auxiliary therapies that can be provided together with mechanical cutting. U.S. Pat. No. '130 does refer to a reciprocating blade (i.e. see claims 4, 5 and 10) but it is not a radially reciprocating motion as is possible with the present invention. The blade has a "relatively straight cutting edge" and the disclosure actually teaches away from a curved blade finding this does not match up well with the shape of lumens (at least in arteries) resulting in cutting into the lumen too deeply in parts to create an uneven inner surface (see Abstract, claim 5, 3:59 and 1:53-2:8.) There is also no disclosure of a rotating, circular, guillotine, or end cutting motion. Rather, the cutting mechanism disclosed in U.S. Pat. No. '130 results from one or more straight edged blades sliding or reciprocating back and forth across a rectangular cutout window at the distal end of a housing, severing atheromas or tissue as it closes the window. The straight cutting blade or blades are as long as the cutout window. Thus, in the cutting position in which the window has just closed, the straight cutting blade (s) completely occlude the window so that no more tissue can enter or exit (3:9-15). In the present invention it is possible for cutting to occur while the lumen (or window through which tissue enters/exits is) is still open, at least in part. U.S. Pat. No. '130 also refers only to electrical activation of the cutting elements while the present invention also includes manual mechanical, pneumatic, hydraulic, and solar-powered electrical activation. More specifically, U.S. Pat. No. '130 describes electrically heating one or more elements on the blade for ablating tissue when adapting the device for prostatectomy (2:9-19 and 7:53-63) and is self described as a device for performing the TURP procedure "in which an enlarged or diseased prostate gland is removed" (2:10-11). This implies the blade must be moved slow enough to allow time for heat transfer to the tissue. A heating element on the blade suggests tissue is ablated with heat rather than mechanically severed. In the present invention only excess core prostate tissue is selectively eliminated and the entire gland need not be removed. At most cutting and heating tissue simultaneously are disclosed. The present invention does not deliver tissue destroying heat to the urethral lining, and is focused on preserving the urethra and prostatic capsule rather than cauterizing it as disclosed in U.S. Pat. No. '130. Also with the present invention the blade can move faster (i.e. higher CPM) Cuts Per Minute since it does not have to wait for heat transfer as its sharp edge alone severs tissue on impact. The Trans-Perineal Core Prostatectomy (TPCP™) and TransUrethral Core Prostectomy (TUCP™) Surgical Systems are focused on removing core prostatic tissue rather than urethral tissue and include several other combinations of simultaneous therapies (including auxiliary drugs, lasers, microwaves, ultrasound, radiowaves, etc.) that may optionally be incorporated to supplement the main treatment via mechanical coring but are not necessary for the invention and/or effective treatment.

Thus, the common approaches to BPH treatment are not minimally invasive and result in trauma to and the removal of the urethral lining, crucial bladder neck musculature, and the prostate's capsule, as well as an unnecessarily large section of the prostate or the entire prostate. Common approaches damage the urethra which results in scar tissue that may occlude the seminal vesicle with the reduction or potential loss of fertility and possibly increase the potential for reverse ejaculation, resulting from the blockage and reduced smooth lining of a natural urethra. Damage to the smooth lining of the urethra caused by these approaches results in increased pain, discomfort, extended catheterization, additional time off from work (recovery), increased dependence on pain medications and extended (and expensive) in-patient hospital stays. The present invention is designed to be used with the prostate access technology of commonly owned co-pending application Ser. Nos. 61/048,427 and 61/086,775 (and their future continuations and other applications claiming benefit of priority to them) to completely eliminate (or at least minimize) urethral damage and destruction of bladder neck musculature, while preserving the prostatic capsule with a small micro puncture in order to gain access to the core of the targeted bulk tissue of the prostatic lobes.

Recent prostate treatment probes have focused on newer energy therapies while an understanding of how to precisely control them to selectively remove tissue remains to be mastered. Mechanical cutting/coring prostate tissue has remained largely unconsidered recently. The reference art that does deal with mechanical cutting atherectomy probes for the prostate is old, crude, and rigid. The present invention refines mechanical cutting and combines it with other therapies to provide a flexible, adaptable device, taking full advantage of advances in the mechanical, biomedical, and electrical arts.

Minimally invasive therapies are not without side effects. A recent study demonstrated the impact of four different types (standard transurethral resection of the prostate (TURP) in 55 cases, transurethral microwave thermotherapy in 34, interstitial laser coagulation of the prostate in 42 and transurethral needle ablation in 42) of BPH treatment on post-treatment quality of life and sexual function. The study found a statistically significant association between ejaculatory dysfunction and an adverse impact on sexual activity following the procedures. However, there was no correspondingly significant change post-procedure in either sexual desire or erectile function with these same therapies. Accordingly, post-treatment sexual dysfunction and the corresponding impairment in quality of life appear to be largely attributable to ejaculatory problems. (See Y. Arai, Y. Aoki, et al. "Impact of Interventional Therapy for Benign Prostatic Hyperplasia on Quality of Life and Sexual Function: A Prospective Study" in The Journal of Urology, Vol. 164, Issue 4, pp. 1206-1211.) Ejaculation loss or severe decrease in ejaculate volume was reported by 48.6%, 28.1%, 21.6% and 24.3% of the patients in the four treatment groups referred to (TURP, microwave, laser, needle ablation), respectively. Thus, there is a need in the art for minimally invasive procedures that do not negatively impact quality of life with reduced or eliminated ejaculation (or changes in volume, pressure, direction, etc.).

Another important consideration in BPH treatment is to address the problem early. This is in contrast to the "watchful waiting" approach that typically coincides with drug therapy while putting off surgery until symptoms become unbearable and conclusively demonstrate irresponsiveness to drugs. The easier and safer the surgical procedure becomes the less it is something to be put off and avoided. There are significant benefits to be obtained in early intervention in the form of preserved bladder muscle tone and function. The longer an individual with a developing hypertrophic prostate waits before having surgery (to remove the hypertrophic portion) the more likely it is the hypertrophic tissue will begin to obstruct the bladder neck which leads to all sorts of complications as the bladder reacts to try and achieve a higher pressure to pass fluid through the constricted neck. These complications include: permanent loss of detrusor contractile ability, involuntary detrusor contractions, partial denervation of the bladder smooth muscle, bladder irritability and instability, early termination of voiding, intermittency of the urinary stream, higher residual urine volume, loss of bladder compliance, and overall bladder mass increase with less muscle tone and more collagen deposition. See Leslie, Stephen W, MD, FACS, (Founder and Medical Director of the Lorain Kidney Stone Research Center, Clinical Assistant Professor, Department of Urology, Medical College of Ohio) "Transurethral Resection of the Prostate" especially under heading "Pathophysiology" as published on eMedicine from WebMD (updated Oct. 3, 2006) accessible at http://emedicine.medscape.com/article/449781, accessed on Mar. 10, 2009. As the body reacts to the obstruction the internal and external sphincters can also be damaged and worn down. The loss of involuntary muscle response that accompanies damage to the internal sphincter generally cannot be reacquired through training (whereas training is sometimes effective to reverse damage to voluntary muscles). Thus, damage to the internal sphincter from waiting too long for surgery and/or from other less selective procedures can cause irreversible reverse ejaculation.

The present invention is designed to remove core prostate tissue to prevent, eliminate, reduce or reverse obstruction of the bladder neck and preserve the natural bladder and sphincter health, muscle tone, and stability to avoid this cascade of potentially irreversible events. The probe is designed to de-bulk by removing the core prostate tissue that is most proximal to the bladder neck in order to maintain the bladder neck's natural ability to contract. The mechanical cutting probe described herein is a preferred means to achieve this since it does not cause the post-removal scar tissue associated with laser, transurethral incision of the prostate (TUIP), and TURP procedures. Scar tissue can enlarge/swell and re-clog the bladder neck to undo the benefits of TURP or LASER procedures. Scar tissue around the seminal vesicle, and the damaged bladder musculature, can be responsible for reverse ejaculation. By reducing (TUCP™) and/or eliminating (TPCP™) the amount of post-procedure scar tissue through a low trauma selective mechanical cutting approach the present invention drastically reduces the potential for reverse ejaculation and post-treatment restenosis and the impact these events can have on quality of life, sexual function, and self-esteem.

BRIEF SUMMARY OF THE INVENTION

The invention provides surgical instruments for mechanically cutting/coring excess or diseased tissue from the core of the prostate gland through TransPerineal Core Prostatectomy (TPCP™) and/or a TransUrethral Core Prostatectomy (TUCP™). The devices and methods described herein are primarily intended to ameliorate the condition of benign prostatic hyperplasia (BPH) by relieving impingement of the gland on the urethral canal, and bladder neck while maintaining the smooth natural linings of the pre-BPH lumens of the urethra and seminal vesicle. The probe was also described in co-pending commonly owned provisional application Ser. No. 61/104,382 entitled "Mechanical coring prostatic atherectomy probe with live aspiration" filed Apr. 28, 2008 of which the benefit of priority is claimed and that is hereby incorporated by reference herein to the extent it is not inconsistent with the present application.

The invention also provides a pathway and method for removing tissue from the cutting area as quickly as it is cut to facilitate a more efficient continuous cutting process. The removed tissue may be temporarily retained in the housing of the probe but is preferably suctioned external to the body immediately after it is cut. In a preferred embodiment, the present invention uses "live aspiration" through continuous suction or mechanical aspiration to provide instantaneous tissue removal that transfers tissue externally to the body as soon as it is severed. "Live aspiration" that instantaneously removes tissue allows much longer continuous cutting sessions since a receptacle in the housing does not fill up and limit the procedure by the need to be emptied. The faster cutting speeds of the coring blades in the present invention facilitate this continuous removal process by cutting tissue more frequently and cutting in smaller segments to ensure the exit pipeline does not become clogged. Since the invention is not dependent on heat transfer for thermal cutting there is no need for coring speed (movement of the blades) to be limited by the time it takes for heat to transfer from the blades to tissue. The sharp edges of the blades and/or burrs alone are enough to severe tissue instantaneously on impact. Tissue removal is provided by a vacuum suction channel that intersects with the cutting area of the instrument. Since the suction is very powerful and applied via linear control during the cutting process the opening in the housing through which a sharp edge on the cutting core interacts with and severs tissue does not have to be closed off or sealed during cutting (such as taught in U.S. Pat. No. 5,571,130 referring to closing off an aperture with existing elements (i.e. blades) with dimensions at least as big as the cutout; i.e. see claims 1 and 4 of that patent). The openings or portals in the housing through which cutting occurs (tissue enters and sharp edges on the core interacting with it) can stay at least partially open while tissue is severed and tissue will not become dispersed (i.e. rebounding off the blades) or lost internally because the powerful suction pulls it out of the cutting zone and body too quickly. The mechanism is also supported by "pinch valves" (that are present on the system's console) that close the line to pressure thus holding any liquids or tissues in the probe or suction tubing until it is eventually collected in the single use surgical cassette for bio hazardous disposal at the conclusion of the procedure. Continuously available suction through at least a partial opening in the housing also quickly cleans up obstructions like debris, smaller tissue fragments, and fluids in the cutting zone for better visualization and sharper cutting with no blade energy wasted on these obstructions. When the cutout window is completely closed (in reference art devices, i.e. U.S. Pat. No. '130 cited above) suction is at least temporarily denied to the region outside the instrument. This temporary lapse of suction may permit tissue fragments in this outside region that have already been severed but not pulled in to scatter. It may also permit fluid(s) to begin to accumulate. Tissue removal is assisted with aspiration and irrigation to keep the cutting pathway and suction channel clear by simultaneous infusion of tissue(s) with saline irrigation fluids while draining them. Irrigation may come from the distal tip at the end of the coring probe body and/or out of the sides in the distal region or from a separate inlet port or catheter independent of the coring probe. Preferably, irrigation comes from the circumference ends and sides of the probe body for faster more efficient flushing and tissue removal. Preferably, irrigation is self-irrigation coming directly from the probe body itself rather than a separate instrument or catheter.

Several embodiments of the present invention are provided which with respect to: (i) the design of the cutting blade(s), (ii) the range of motion (ROM) or movement pattern(s) of the blade(s), (iii) the power source used to activate or actuate motion of the blade(s), and (iv) the availability of optional auxiliary, supplementary, or complementary therapies to be provided from the same instrument simultaneously or sequentially (including alternating and cyclical) with the main mechanical cutting function. In some embodiments, a multi-modal cutting probe is provided that allows the user the option(s) of: cutting with more than one blade, selecting a different type of blade, cutting from more than one location on the probe body, moving the blade(s) in more than one range of motion (ROM) or pattern, powering the blade with one of several different power sources, adjusting the speed of the blade(s)' cutting motion, selecting between continuous and intermittent cutting, and/or supplementing mechanical cutting with one or more secondary therapies (i.e. ultrasonic vibrations) all from the same instrument.

The present invention is designed to function as part of a minimally invasive surgical system and approach that removes the minimum amount of prostate tissue (typically around 33% volume or 20 grams for an average 60 gram sized prostate) necessary to healthily restore the natural flow of urine from the bladder through the urethra adjacent the prostate while also minimizing and/or eliminating urethral trauma (depending upon your choice of our technology: TUCP™ or TPCP™) and scar tissue to minimize pain, shorten procedural recovery time, and maintain normal bladder neck musculature/function, seminal vesicle ejaculation, reproductive potency, and delivery of semen.

A method of removing prostate tissue can be summarized in three steps: (1) access, (2) removal, and (3) hemostasis. The atherectomy probe of the present invention is part of the removal step. The access and hemostasis aspects are addressed in more detail in commonly owned co-pending application Ser. No. 61/086,775 and Ser. No. 61/120,115 and future applications that will claim the benefit of them. To the extent these applications (61/086,775 and 61/120,115) are not inconsistent with the present application they are hereby incorporated by reference herein. The cutting probe is designed to be used with and without several other individual components including: a protective delivery sheath (i.e. balloon and/or lubricated sheath to protect the insertion lumen such as urethral canal, rectal canal, perineum region, or laporoscopic, umbilical, or other endoscopic passageway), a lancet/trocar blade/stylet system that provides access to the prostate for the probe, fiber optic camera visualization and illumination components built-in to the probe or as part of a separate probe, poly ethylene glycol (PEG) plug or other hemostatic agents, tamponading balloons, a sealant and/or hemostat that may be again added if necessary, a hemostatic agent delivery device, an identification cassette and/or card for attaching to the console, and a surgical console that contains one or more pinch valves to control linear aspiration, fluid irrigation and residual vacuum that builds up in the flexible tubing lines connected to the probe's vacuum suction system. These additional components can be used with the probe as needed and are not all needed all of the time.

In the "access" phase, optionally, a pre-lubricated protective delivery sheath that is pre-labeled with depth dimensions ("measurement markers") is inserted through the urethral canal in a deflated, tubular-rolled condition. Preferably, the protective delivery sheath has a clear or transparent distal tip and can be inserted over a guidewire or pushed with an insertion device. Once the protective delivery sheath is inserted to the desired depth within the body (as may be determined based on a reading of the measurements on the sheath's outer cover, and anatomical visualization is confirmed via the illuminated fiberoptic camera) the cover peels away and inflation of the protective delivery sheath begins. When used on the sheath, the "measurement markers" inform the physician and medical personnel how deeply the sheath has been inserted within the urethral canal. In alternative methods, access may be made through other entries and the "measurement markers" would indicate depth within other parts of the body: the rectal canal for transrectal insertion, the perineum for transperineal approaches in which dilating or end-cutting trocar(s) could provide a working channel and clear access to the prostate's capsule with a minimally invasive introduction, or could assist with providing depth within the abdomen for laporoscopic entry or umbilical entry, or insertion depth in any other part of the body for endoscopic or open surgical entry anywhere.

A pre-lubricated delivery sheath is not essential to the present invention but is included in some embodiments of the BPH system/kit. It may also be used in other passageways when non-urethral approaches are used. The sheath involves an extra step before introducing the coring probe but for very sensitive patients or those with a damaged or especially narrow passageway the enhancement it provides in patient comfort and increased hygiene may be worth the extra time it takes. The sheath increases hygiene by providing an extra barrier between the outer surface of the probe body and the inner wall (or damaged inner wall) of the passageway. If the patient has a healthy access passageway (i.e. urethral canal) and/or the outer surface of the probe itself is sufficiently smooth the sheath can be avoided. According to some embodiments, the probe itself can incorporate additional features on its outer surface in order to facilitate its introduction and better justify avoiding the sheath. These additional features may include a sterilized non-metal spongy outer layer with some resistance and shock-absorbance, the gradual elution of lubricants stored within, a flexible or partially flexible shaft, etc. If the coring probe's outer surface includes some of these additional features the pre-probe delivery of a lubricated sheath might be avoided even in sensitive patients with compromised passageways.

Preferably, measurement markers that designate depth are also provided directly on the probe body itself. Like the sheath markers, these markers will let the physician know how deeply the probe is within the access passageway (i.e. urethral canal) and are especially important if the sheath and probe become misaligned or if the sheath is not used. Additionally, since the probe goes on past the canal to enter the lobes of the prostate, the markers are especially helpful here for the physician to determine whether the coring probe has been inserted sufficiently deep (i.e. before and during activation of the mechanical coring operation) to reach the prostate's core while avoiding unnecessary penetration. By reducing uncertainty, the markers inhibit overly aggressive coring and thereby assist to preserve a maximum amount of healthy prostate tissue. Typically, around 66% or two-thirds (usually around 40 grams) of the prostate can be left intact.

When the protective delivery sheath is used, initially, the sheath is inflated only to nominal pressure so that it unrolls from its deflated, tubular-rolled insertion condition and expands to occupy the entire natural diameter of the urethral lumen.

With the protective delivery sheath in position at nominal pressure, the illuminated fiber optic visualization system should be connected to the console. Fluid delivery and aspiration ports should also be connected to the console. The surgical console can control infusion via a pump or alternatively, an intravenous (IV) infusion bag (i.e. on a pole) and can control infusion via gravity with a pinch valve or manual adjustment to the IV tubing set. Preferably, a pump is used for fluids that must be delivered with forces that cannot be achieved with gravity alone. The IV pole may be actuated via a footpedal that raises or lowers the IV pole to adjust irrigation or infusion of a coolant fluid (i.e. cooled saline) within the sheath or within a light pipe camera system.

The TransPerineal Core Prostatectomy (TPCP™) will be initially started in clinic with pre evaluation sizing and mapping of the target areas that need to be cored using ultrasound imaging to create a strategic map. During the procedure the transrectal ultrasound system will be deployed to visualize and confirm the strategic removal of core prostatic tissue. Based upon the measurements confirmation, the "Surgical Procedure Pack" will be opened. The contents will include the disposable products listed: blade, trocar set, cassette with tubing lines, atherectomy probe, transrectal ultrasound probe cover with safety technology, urethral micro camera with safety technology for live visualization of urethral decompression and sub tissue probe visualization via LED (Light Emitting Diodes).

The physician will start with insertion of the transperineal or transurethral camera and transrectal ultrasound for visualization. The camera may be provided directly on the probe body itself. The transperineal incision will be based upon the Surgical Grid that will provide the desired/strategic coordinates to access the target core tissue that was diagnosed during pre surgical analysis.

Next, with the fiber optic system in position, the anatomic landmarks for the removal of bulk tissue within the prostate should be again ascertained (i.e. parts of the medial and posterior prostate that appear to be putting the most pressure on the urethra, especially around the bladder neck). Optionally, a fiber optic camera and a source of illumination (i.e. light emitting diode (LED)) for direct visualization can be built into the shaft of the atherectomy probe itself. Alternatively, the fiber optic camera and light source (i.e. LED) may be part of a separate probe or included in a light pipe system extending through either a separate probe or as a channel along the atherectomy probe's shaft or within the atherectomy probe's lumen. The illuminated camera system and the atherectomy probe may also both be elements along channels in the body of an endoscope.

After determining the pathway coordinates the physician creates a small skin incision in the perineum. The physician will then insert the trocar system with the assistance of transrectal ultrasound guidance and the Surgical Grid to non-invasively dilate the perineal tissue and guide the trocar to the prostate's capsule. Once trocar dilatation has created a sufficient working space, the micro-puncture tools are used to create the access into the prostate's core through a tiny opening in the prostatic capsule that preserves the capsule's basic shape and structure. The blade is then removed and replaced with the Radial Reciprocating Atherectomy Probe ($R^2AP$ or "RRAP"). The probe is inserted through the Surgical Grid and activated upon safe anatomical confirmation.

A stylet blade is then inserted into the urethra and is activated (similar to an ink pen with a pushable button) to deploy the blade that is used to create the "micro puncture" in the urethra wall and then extends to create a second micro puncture of the prostatic capsule of the medial lobe's core to create "working space" for delivery of the atherectomy device. In addition or as an alternative to micropuncture, dilation can be used to create the working space, including with progressively dilating trocars and other means beyond traditional dilation balloons.

Preferably, to assist in properly placing the probe, a grid system is utilized similar to how a guidance grid can be utilized to insert radioactive seeds into the prostate to kill tumors with brachytherapy. The grid system comprises a physical template with variably sized holes and optionally, is performed under ultrasound guidance for better accuracy. The template holes are large enough to accommodate the coring probe shaft and the variable sizes used in conjunction with a tapered shaft on the probe allow a safer insertion with depth control. When a coring probe with a tapered shaft is inserted in the bigger holes on the template it will reach more deeply then when it is inserted in the smaller holes. Ultrasound guidance can be used to inform the best holes in the template to use in order to reach the best coordinates (X,Y,Z) for mechanical coring therapy.

The Surgical Grid provides guidance similar to other easy to use designs that are known to those in the art of treating prostate cancer with brachytherapy and toxic seed placement into cancerous prostatic tumors. The system has alphabetic columns and numeric rows with restricted corresponding open ports that only allow certain predetermined targets and tissue depths based upon the I.D. of the grid and the tapered shaft of the probe. The probe's tapered shaft also includes depth markers that can be visually seen by the operator. This technology ensures safety with reduced or eliminated patient injuries related to introducing the probe beyond the bladder neck and damaging the bladder, or delivering the probe too far in another direction which could cause a transrectal perforation.

To further guide the probe in reaching the prostate and staying within the perineum an alarmed sensor system can be provided that provides positive and/or negative feedback to signal to the operator that the probe is placed properly or approaching an unintended structure and off-track. A sensor (i.e. transmitter) on the probe tip may communicate with one or more sensors (i.e. receivers) on other probes or attached to other parts of the body to provide positioning feedback. For example, a sensor on an ultrasonic rectal probe cover may receive a signal from the transperineal probe tip transmitter and let the probe operator know if the transperineal probe gets too close to the rectal canal.

The "removal" phase begins with the insertion of the atherectomy probe. The atherectomy probe is inserted alone or optionally, through the protective delivery sheath, after the probe is connected to the console (including the power supply).

With the RRAP in position the atherectomy probe is activated and core prostatic tissue is removed under live continuous observation and collected into the clear disposable cassette on the surgical console. Meanwhile, the transurethral camera actively searches for decompression of the predetermined treatment areas within the prostate throughout the coring operation and tissue removal process. This core debulking includes targets such as the bladder neck, median lobe, and other areas that are determined during a pre-surgical analysis and recorded on a pre-surgical worksheet.

After the target areas show visual decompression, and the cassette system shows a visual estimation of target tissue removed, the procedure can be completed or the areas may be re-treated again via the same prostatic micro puncture. Ultrasonic pictures are suggested for procedural documentation to measure pre and post TPCP™ surgical results demonstrating a volumetric reduction. Pictures can be taken immediately after surgery and during a patient's follow-up in the days to come to monitor healing progress.

Once the procedure is completed the atherectomy probe is removed and the micro puncture to the prostate's capsule is evaluated. A few minutes of direct pressure is applied to assist with hemostasis. A hemostatic agent may be applied to achieve hemostasis if necessary. Many products may be used at this time, such as fibrins, glues, thrombins, and as a last resort cautery.

With the target location(s) in view the atherectomy probe is inserted into the core of the lobe and then activated to perform a "core prostatectomy" removing target bulk tissue regions of the medial and posterior prostate. Preferably, the coring procedure should remove approximately 30% of bulk tissue from the medial prostate and at the surgeon's option it may also remove approximately 20% of bulk tissue from the posterior prostate.

Following the initial de-bulking of the core prostate in the anterior, medial, and/or posterior lobes, the urethral canal should be inspected for adequate urethral diameters to ensure the normal flow of fluids (bladder, semen, etc.) post-procedure. If there is still limited flow or the flow of materials is inadequate, additional core prostatectomy therapy should be performed to remove the excess bulk tissue and constrictive pressures until flow is restored.

In its broader aspects the present invention is not limited to a mechanical atherectomy probe and includes the introduction of any device or means of therapy (i.e. ultrasonic energy, harmonic scalpels, lasers, microwaves, needle ablation, etc.) to de-bulk the prostate's core in which the core is reached from a transurethral, transperineal, transrectal, laporoscopic, transumbilical, endoscopic, etc. approach through a micropuncture and/or progressive dilation. The mechanically coring probe described herein is a preferred device or means of therapy to incorporate in these access methods.

The blade used to create the micropuncture and method of its use provides self-sealing wound architecture embodied in a tiny gateway to remove problematic hypertrophied core prostate tissue while minimizing the impact of the procedure on the majority of the healthy prostate tissue. As a complement or substitute to micropuncture, progressive dilation can be used to gently and gradually expand a working space within the prostate without as much cutting/dissecting as traditional surgery. Dilating rather than cutting preserves the healthy prostate. The smaller cuts made with micropuncture access also preserve prostate compared to more traditional cutting and broader application of energy therapies (radiowave, microwave, etc.). Progressive dilation can be accomplished by sequentially inserting a series of larger and larger co-axial dilators over a central sharp trocar or guidewire. The cutting edges of the mechanical coring probe also provide self-sealing wound architecture that minimizes the amount of post-procedural scar tissue formation so that the volumetric reduction from removal is not undone by aggressive scar tissue growth. Optimally, the wound architectures created by the micropuncture, dilation, and mechanical coring instruments are "self-sealing" in that they preserve the prostate to such an extent and have such a limited region of impact that hemostatic devices and tamponading balloons can in many cases be avoided completely as the small openings will naturally close. Natural closure or closure with minimal hemostatic devices can provide an advantage over devices and methods that seal with heat. In sealing with heat the urethral lining will inevitably incur some damage. Using self-sealing natural closure or non-heating hemostatic devices and methods this damage can be avoided.

If the flow through the urethral canal is adjudged to be adequate, then the "hemostasis" phase of the procedure can begin. As mentioned, in some cases, due to the small incisions and self-sealing cutting devices and methods hemostasis occurs naturally shortly after removal of the instruments and additional plugs, sealants, and tamponading balloons are not needed. Application of manual pressure by the surgeon can be used to stimulate this natural hemostasis.

When necessary additional hemostatic agents can be used such as the insertion of a poly ethylene glycol (PEG) plug into the cored lobe. Preferably, the PEG plug is deployed by retraction of a sheath on a delivery device. Once the plug is properly placed, inflatable tamponading balloons may be used over it to direct pressure evenly and to create closing pressure onto the PEG plug. This multi-component system in the medial lobe's core achieves hemostasis from both direct pressure tamponade and activation of the PEG plug. The balloons are inflated with an incompressible coolant fluid (i.e. cooled saline solution) for reduced inflammation and pain, reduced bleeding, improved stability, and greater patient comfort and satisfaction. The coolant fluid balloon tamponade prosta plasty system should remain in position for approximately 3 minutes to provide an adequate tamponade effect. After the first 3 minutes the site should be inspected for stability upon minimal deflation. If bleeding is still present, the balloons should be re-inflated to full inflation and the tamponade should remain in position for approximately another 3 minutes. This seal, hold, and inspect cycle should continue until the atherectomy site demonstrates stability showing no further bleeding. Minimal drainage is permissible. As necessary, other sealant products (i.e. gels, powders, patches, plugs, etc.) can be administered (i.e. adhered, applied, injected, inserted, plugged, sprayed, etc.) after removal of the balloon tamponade system, including: thrombins, fibrins, fibrin glues, gelatins, platelets, etc. derived from human, bovine, porcine, synthetic, etc. sources. Before using such sealant products the physician should refer to the individual package inserts for indications and precautions.

A supplementary, complimentary, and/or alternative means to achieve hemostasis is to use a microscopic end cauterizing probe to supply energy to seal the site. The probe can be bipolar or monopolar and it can emit any one of several forms of energy to accomplish such sealing: electrical, laser, microwave, radiofrequency, resistive heating, ultrasonic, etc. The probe could be inserted into the body through the protective delivery sheath or without the sheath if the probe's outer surface and structure are sufficiently atraumatic. The probe should be directed through the micro puncture site in the urethral wall and prostatic capsule to reach the core prostate. At the core prostate, the cauterization probe should be activated briefly to achieve hemostasis and seal the zone from which bulk tissue was removed.

BRIEF DESCRIPTION OF THE SEVERAL VIEWS OF THE DRAWING

FIG. 16 shows how the light sheath with extruded grooves therein conveys infusate all the way to the distal tip of the instrument with the light sheath turning into a lens at its distal tip and tightly wrapped with a thin opaque cover with venting ports for aerating the infusate passing through both the light sheath and opaque cover.

DETAILED DESCRIPTION OF THE INVENTION

Figure 1:
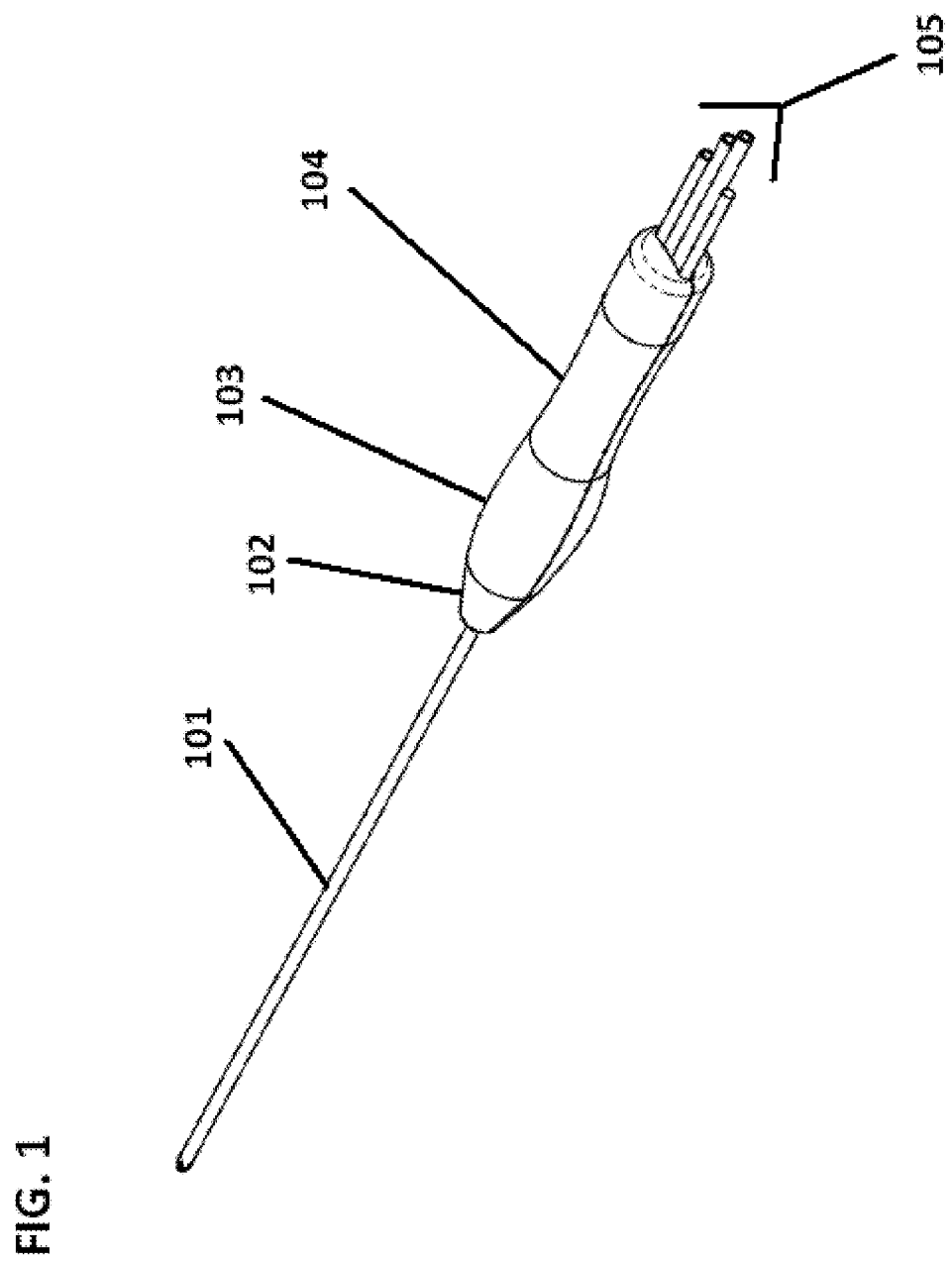
FIG. 1 shows the entire mechanical coring atherectomy probe of the present invention looking from the proximal towards the distal end.

The atherectomy probe of the TransPerineal Core Prostatectomy (TPCP™) system and the TransUrethral Core Prostectomy (TUCP™) system has one or more cutting edge(s) provided in a distal region of a cutting core within a housing. Both the cutting edge and the cutting core should fit within a circular instrument lumen. The cutting edge may be in the form of a blade or any other design. The cutting edge may have any one of several shapes so long as at least some edges of the shape are sharp enough to mechanically cut, miniaturize, and release tissue with minimal effort and minimal exertion of contact pressure. For example, the blade(s) may be linear, V-shaped, X-shaped (criss-cross), U-shaped arch, triangular, rectangular, hourglass, circular with sections (like pie slices) missing, rotating bur (also burr; as used herein "bur" or "burr" of either spelling also refers to and includes the term with the other spelling), etc. The edges of the blades are preferably oriented perpendicularly or at an angle (i.e. diagonally) to a longitudinal axis of the probe body. However, in end cutting embodiments the edges may be parallel to the longitudinal axis of the probe body, pointing outward from the distal tip. For embodiments in which two or more cutting edges of the blades come together to cut, the edges should be parallel to one another (or at least parallel in segments but need not be straight) and patterned to match-up (corresponding) like pieces of a puzzle. However, only one cutting edge is necessary and this one edge may operate by supplying pressure to tissue against the probe housing acting as a buttress instead of coming together with another edge. A singular cutting edge could also come together with another non-sharp moveable element that serves as a moveable buttress rather than a cutting edge. Alternatively, a buttress for a cutting edge is not necessary as the cutting edges may be sharp enough to sever tissue instantaneously on impact by shear mechanical force (high speed). Pointed barbs, burs/burrs, triangular blades, wires or blades etc. may simply protrude from the instrument body to interact with tissue unilaterally without an opposing buttress.

According to a preferred embodiment there is also a stationary (non-moving) partial "hood" that partially covers the moving blades and shields the cutting zone. The hood provides added stability and safety by reducing or eliminating the probe's desire to move back and forth. Additionally, the hood allows the probe to be placed within close proximity to anatomy that is not intended to be damaged or removed (non-target anatomy) without trauma. The hood will provide protection from the cutting mechanism for those situations.

As another safety feature, the linear control of aspiration can be used to minimize the aggressiveness of suction and tissue attraction to the blade. In conjunction with the hooded tip, linear aspiration provides excellent surgeon control. The hood may or may not have sharp edges to assist with cutting as well. The blade(s) mounted on the cutting core may protrude from one or more openings or portals in the housing to interact with tissue. Any number of openings with any shape may be provided. For example, see FIGS. 8-10 and FIG. 12 showing an embodiment with four gum-drop shaped openings 122 in the housing with its protective dome-shaped cover or hood 121. The opening(s) 122 within the housing may be positioned at the distal tip and/or along one or more lateral sides in a distal region (the latter arrangement is shown in FIGS. 8-10 and FIG. 12). The inside edges of the openings or windows may be sharp such that as tissue is squeezed through an opening and pressed against the inside edge(s) by the blade it is cut from more than one direction by both the window's inside edge and by the blade. In a preferred embodiment, there are at least two openings in the housing to provide dual port or multi-port cutting. In a most preferred embodiment there are four openings for a "quad port" design. Increasing the number of openings or cutting ports has the advantage of providing multiple edge points for more opportunities to shear cut tissue. As a result there are a greater number of smaller shear tissue cuts. Many small tissue cuts reduces the likelihood of clogged aspiration lines and also reduces the likelihood of the probe becoming stalled in thick, dense tissue, as compared to fewer large tissue cuts. In one embodiment, at least one opening in the housing is at a distal tip and at least one opening is along a lateral side to provide the option of either or both of end-cutting and side-cutting action. In dual port and multi-port embodiments in which the cutting core can interact with tissue to sever it at more than one location the cutting action in different portals can be performed alternatively, sequentially (including alternating or cyclical), or simultaneously. Additionally, when there is more than one portal or opening in the housing the cutting style or mechanism at each portal/opening can be the same or may be different. FIGS. 8-10 and FIG. 12 show a quad port embodiment with four lateral portals and radial reciprocating side-cutting at all portals. However, several other variations are also within the intended scope of the present invention. For example, there may be two lateral portals with guillotine side-cutting in one portal and radial reciprocating side-cutting in the other portal. Another embodiment may have the aforementioned two portals (guillotine lateral and radial reciprocating lateral) with an additional distal cutting portal doing circular end-cutting (i.e. such as with a pointed burr).

The characteristics of the openings and the blades can be adjusted as needed to achieve a preferred cutting style. For example, the openings can be made larger or smaller with thinner or thicker struts. The sharpness of the blade and the angle at which the blade passes through the opening to contact and severe tissue can also be adjusted. Preferably, the inner cutting edge of the blade is sharp enough to easily sever tissue upon contact.

When there is more than one lateral portal the portals may be lined up axially (i.e. in a row) along a longitudinal axis of the probe body. When the portals are lined up axially their radial locations about the periphery of the probe are identical. Alternatively, more than one portal may be lined up radially (i.e. in a circle) around the periphery of the probe body. When the portals are lined up radially their longitudinal positions from a distal or proximal end of the probe body are identical. Multiple cutting portals may also be offset (not lined up) axially and radially such that they are randomly staggered or form a pattern such as diagonal, zig-zag, helical, etc.

The cutting core of the present invention has at least one sharp edge for severing tissue. Multiple sharp edges may be provided. The sharp edges may be provided in the form of blades with a linear edge or in any other manner sufficiently sharp enough to sever tissue. In an alternative embodiment, the sharp edge may be in the form of one or more piercing distal tip(s) on one or more pointed barb(s) or burr(s). When the sharp edge is provided by a blade the edge may be flat, smooth, and straight or it may be jagged and textured.

According to a preferred embodiment, the sharp cutting edges (i.e. blades, barbs, burrs) are extendable through a push-button actuation mechanism similar to a push-button ball point pen. With this mechanism the push of a button functions to extend the cutting edge(s) and/or to retract the housing covering the cutting edge(s). According to some embodiments, multiple pushes of the button can incrementally adjust the degree of extension of the cutting edge(s) (i.e. the length of the blade). When there are multiple cutting edges at different openings/portals in the distal region of the probe housing they are preferably independently extendable/retractable with multiple push-buttons and a button corresponding to each cutting edge or group of cutting edges.

The direction, pattern, and range of motion (ROM) for the blade may also vary between embodiments of the present invention or between modes in any single embodiment of the present invention and in any single instrument. One such cutting pattern is guillotine in which the sharp cutting edge of a blade descends to sever tissue stabilized between the actuating blade and a wall or other part of the shaft which creates a shearing effect for a smooth cut edge. The guillotine cutting pattern operates similar to a paper cutter in embodiments in which the buttress base (i.e. wall of shaft or another part of shaft) is straight and parallel to the blade. This planar slicing mechanism (guillotine) can be side-cutting when it occurs on a lateral side of the device or a modest form of end-cutting (positioned at a distal end but not protruding).

Another cutting mechanism is radial reciprocating in which the blade moves in an arc. The blade rotates in an arc from left (counterclockwise) to right (clockwise) motion (or vice versa) and can cut on one side or the other or both as desired. Generally, but not exclusively, the sharp edge of the blade comes down vertically (distal to proximal or vice versa along a longitudinal axis of the instrument body) for guillotine and horizontally (around a longitudinal axis of the instrument body) for radial reciprocating.

In a radial reciprocating pattern the blade moves radially throughout a variable bounded range (i.e. 30 degrees, 45°, 60°, 90°, 120°, 135°, 150°, 180°, 210°, 225°, 240°, 270°, 300°, 315°, 330°, 360° etc.). The maximum range of rotation would be a complete circle of 360 degrees. Once the blade reaches the bound of the motion range instead of continuing on in the same direction (right/clockwise or left/counter-clockwise) it changes direction and re-traverses the same path in a different direction.

A third mechanism for cutting is a circular motion pattern similar to the movement of a drill head. In a circular cutting pattern the blade rotates radially but continually moves further and further in the same direction (i.e. right/clockwise or left/counter-clockwise). The circular atherectomy cutter spins inside of the shaft and cuts tissue by having the sharp blade or bur/burr portion engage the tissue against the shaft or with direct pressure to sever and miniaturize for aspiration and removal.

A fourth mechanism for cutting is end cutting. End cutting involves blade(s) situated at or protruding from a distal most tip of the instrument. Typically the blade(s) extends straight or at an angle between an orientation parallel to the instrument body and an orientation perpendicular to the instrument body (i.e. oblique or transverse). The blades may resemble those at the base of a blender machine in the kitchen. The range of motion or cutting pattern of the protruding blades in an end cutting device may be reciprocal, radially reciprocal, or circular/rotating. In an alternative end cutting embodiment similar to typical side cutting the blade(s) may simply be situated at a distal end of the instrument rather than protruding from it. The blades may traverse a distal cross-section of the probe lumen to perform with reciprocating or guillotine cutting styles.

The power or pressure source that activates and actuates the blade motion can also vary between embodiments or between modes in a single embodiment. To some extent the power or pressure source to be used depends on the motion pattern desired for the blade. Some motion patterns work better when actuated by certain sources of power or energy than other sources. Regardless of which power source or actuation means is used to drive the cutting blade, all actuation takes place at the proximal end of the instrument outside the body of the patient. The actuation process occurs in the handpiece and the cutting action/motion is delivered down the shaft toward the targeted bulk tissue in which it is engaged by its operator. There may be a power generator in the handpiece to initiate the actuation process. Preferably, the power generator produces pneumatic or electrical energy to drive the cutting core.

According to an alternative embodiment, the power generator is an ultrasonic generator that operates at high frequencies in the range of 50,000 Hz. This ultrasonic generator obliterates tissue into tiny morcels of emulsified "mush" that can be easily removed via aspiration. The delivery of ultrasonic energy to the core prostate can be used as a substitute, a compliment, or a supplement to other forms of core prostate removal (i.e. mechanical cutting). The use of mechanical cutting before or during ultrasonic energy application should accelerate the emulsification process by creating smaller particles for the ultrasonic energy to act upon, thereby concentrating its effects. Ultrasonic energy would be used in much the same way as phacoemulsification is in cataract surgery to obliterate a thickened lens. "Live aspiration" would evacuate the obliterated morcels/emulsified "mush" through one or more openings in the distal tip of the probe via a continuous process of irrigating (via end and/or side ports) and aspirating (or suction). The ultrasonic generator may incorporate microprocessor-controlled fluid dynamics based on a peristaltic or venturi type of pump.

According to a preferred embodiment the power source that drives the probe is pneumatic. In pneumatic actuation the exhaustion or decompression of a gas (i.e. air) or a compressed gas (i.e. nitrogen) is used to drive pistons that transfer their energy into blade motion and actuation. Pneumatic actuation is appropriate for guillotine, radial reciprocating, circular/rotating, and/or end cutting action. A most preferred embodiment uses pneumatic power to drive radial reciprocating blade action.

Another power source is hydraulic. In hydraulic actuation the motion of a liquid (i.e. water) is used to drive the motion of the blade.

A third power source is electric. Electrical energy can come from a conventional power outlet. The instrument preferably can run off of alternating (AC) or direct (DC) current. The electric system can also be battery powered. Electric energy is ideal for powering a blade in a circular cutting pattern.

A fourth power source is solar energy. The cutting probe may optionally be designed to charge upon exposure to solar radiation. Solar energy is an indirect power source for the cutting element in that it is first converted to electrical energy.

A fifth power source is manual mechanical energy as controlled by an operator. This manual source can be used for any of the cutting patterns but may be easier to administer with some than others. For example, it may be easier for a user to turn a nob back and forth for radial reciprocating motion than to continually readjust one's grip and keep turning a nob in the same direction as for circular cutting. Nonetheless, in a well designed device manual mechanical operation by the user could be used to easily and smoothly actuate any cutting pattern.

In any of the aforementioned embodiments (any type of blade, any range of motion, any power source) the instrument is designed with various channels. Some of these channels are necessary and used for basic functions such as removal of severed tissue while others are optional and used for auxiliary or supplemental therapies.

The basic function channels are for: tissue cutting, tissue removal, live active suction or withdrawal of fluids, self-irrigation or flushing with fluids, and drainage of fluids. The tissue removal feature of the present invention is designed with a pathway large enough to transfer an evacuation force strong enough (i.e. vacuum suction, peristaltic pump, piston system, venturi vacuum, etc.) to keep pace with the rate at which tissue is severed, and with the volume at which severed tissue is generated to avoid accumulation of necrosed tissue. Prompt removal of necrosed tissue keeps the cutting mechanism strong, efficient, and maintains optimal direct visualization as well as keeps the exit pathway clear and effective, thus reducing infection, internal redistribution and the potential risk of complications associated therewith. Irrigation provides consistent smooth aspiration and reduces air locks to keep the aspiration and tissue removal process running interrupted.

Channels may also be provided within the probe body to deliver pharmaceutical drugs and other therapeutic medicinal agents directly at the target site. Examples of drugs that might be delivered include antibiotics to prevent infection, and antiproliferatives to control scar tissue formation.

In an alternative embodiment, other channels in the instrument may be used to provide a secondary or alternative therapy that augments the primary mechanical cutting therapy. The secondary therapy may be one that is powerful enough to be used independently to reduce the size of the prostate and to relieve the symptoms of BPH. Performing a little mechanical cutting action to expose the more sensitive and vulnerable inside of tissue and then applying the secondary therapy may be more effective than applying the secondary therapy alone. Mechanical cutting can be used to identify and literally carve out a target site so that any other therapies can be used in a reduced amount and applied with precision focus, reducing their impact on nearby healthy tissue. A preferred complementary therapy is heat therapy to provide tissue cauterization, coagulation and hemostasis before, during, or after cutting. Heat therapy may be provided by heating the sharp mechanical cutting blade(s) (i.e. heated end cutting bur(s)/burr(s)) such as by adjusting diathermy controls on a central console.

As a preferred alternative or supplement to diathermy for a heated blade, hemostasis is provided by a hemostatic agent deployed from a retracting sheath on a delivery device. A preferred hemostatic agent is a PEG plug. Preferably, the delivery device has an ergonomic handle with slots for a medical operator's fingers and thumb to avoid instrumentation slippage. The hemostatic agent delivery device also has a safety clip to prevent premature and/or accidental deployment. The inflation of tamponading balloons (via prosta plasty system) should follow placement of the plug for extra sealing reinforcement and more evenly distributed pressure upon the plug and throughout the cavity.

In some cases, using the minimally invasive techniques described herein, hemostatic devices such as tamponading balloons and sealants should not be necessary. Using either the micropuncture or progressive dilation approaches to access the prostate maintains the natural prostatic capsule so that it can incarcerate the surgery zone and naturally control bleeding. If the incision is small enough and dilation gentle enough (and depending upon the patient) hemostasis will occur naturally upon removal of the instruments due to preservation of the capsular shape of the prostate. As the prostate returns to its natural shape upon removal of dilators bleeding should subside. A surgeon's digital application of direct pressure through the rectum can be used to initiate natural hemostasis in the prostate while waiting to see if auxiliary hemostatic devices are going to be necessary.

When auxiliary hemostatic devices (balloons, sealants, plugs) are used, it will be found that the small opening created with the micropuncture and/or the small cavity formed through progressive dilation to provide access to the prostate and shape a working space is just the right size to accept a hemostatic plug. Sometimes this small opening and working space will close-up on its own as instruments are removed and the preserved prostatic capsule quickly rebounds. However, in some patients with less elasticity in their tissue, blood that doesn't clot easily, and/or in those with diseased prostates in which additional prostate tissue must be removed the rebounding process is slow and/or incomplete requiring the use of hemostatic devices to control bleeding at least in the short-term until natural healing can occur.

In one embodiment, the body of the atherectomy probe is flexible to navigate the natural bodily lumens that are typically somewhat tortuous. This flexibility may be provided by the material from which the body is made including soft metals with shape memory (such as nitinol, cobalt, and chromium), plastics, or elastomeric polymers. The flexibility may also be provided by a segmented body capable of angular and/or radial rotation at the segment junctions. The individual body segments may be straight or curved to create sharp turns or smooth waves when they are bent. The blade itself may optionally be made flexible unless locked rigid. This would reduce damage done from inadvertent instrument movement when the blade is exposed but not locked. Flexibility in the blade would allow it to spring back upon compression into tissue rather than piercing right into tissue.

The blade itself may be made adjustable independently from the instrument body. For example, the position of the blade within the body may be controlled to move the blade from a position protected within the shell of the housing to the distal end of the body for sheltered cutting and optionally, to extend past the distal end of the body for exposed cutting. Thus, the blade may be longitudinally and/or radially extendable. Preferably, this is accomplished through a push-button actuation mechanism with a locking option (in either retracted or extended position) and a quick release safety feature to immediately collapse the blade from a locked extended position.

Anatomical dimensions vary from person to person including the diameters of the urethral canal, bladder neck, and seminal vesicle. Accordingly, it would be useful to be able to adjust the diameter of the instrument and the angle and/or length of the blades in situ. The objective is to ensure that there is adequate pressure between the blade of the instrument and the tissue when the instrument is in position to cut a target site without any pressure when the instrument is being inserted to or withdrawn from the target site. One way to achieve these variable diameters of the atherectomy instrument and its blades is for the distal end of the probe to include a flanged segment that tapers outward to cut and can be retracted back inward for passage. The flanged segment may retract radially (by turning) and/or longitudinally (i.e. in a telescopic manner).

Although the mechanical manipulation of the cutting blade and instrument body will be sufficient in most cases to provide the necessary traction against tissue for cutting, additional devices and methods may be utilized to enhance the contact pressure between the sharp end of the blade and the tissue which is to be cut. One device for creating additional pressure between the cutting blade and tissue is an expandable balloon. The balloon can be part of a separate balloon dilation instrument or it may be part of the atherectomy probe itself. In a preferred method, the balloon would be deployed along a side of the atherectomy probe on a side opposite the action of the cutting blade such that its inflation pushes the cutting blade into tissue. With the balloon outside the body of the probe it does not interfere with the tissue removal and other channels (i.e. irrigation, drainage, etc.).

An optional element that may be included on the probe is a means for detecting and characterizing tissue. This element would be capable of distinguishing target tissue (i.e. unhealthy hyperplastic regions) and then characterizing the target tissue (i.e. density, thickness/depth, etc.). The detection and characterization means should be employed prior to beginning cutting in order to direct the modalities (i.e. blade size, sharpness, cutting pattern, rotations per minute, suction level, etc.) chosen for the cutting operation. One such means could be an ultrasonic sensor that emits sound vibrations to determine tissue depth.

The present invention offers a treatment option for BPH without burning lasers, without rectal probes, and without mass ultrasonic usage. Since electrical or pneumatic energy is used to mechanically drive the sharp cutting core of the atherectomy probe, the system can be made compactly as compared to BPH systems that require large complex systems to generate microwaves, radiowaves, ultrasound, vapors, heated water, etc.

The removal of only modest amounts of the medial and posterior prostate can adequately reduce impingement within the urinary and seminal channels. The post-procedure improvement results in the expansion of the channels substantially back to their pre-BPH diameters with a preserved, healthy, and smooth urethral lining for a natural release of urine and seminal fluids.

The procedure begins with the insertion into the urethra of a retrievable protective delivery sheath (i.e. inflatable balloon and/or highly lubricated sheath). The inflated protective delivery sheath serves as a channel to create space for and protect the urethral wall from both the visualization probe and the atherectomy probe.

The atherectomy probe also fits within the protective channel formed by the inflated protective delivery sheath. The focused, micro invasive design of the present invention requires that only the smallest instruments feasible be utilized. The outer diameter of the cutting atherectomy tool is 1 mm to 4 mm. In a preferred embodiment, the outer diameter of the cutting atherectomy tool is 2.778 mm. The atherectomy tool comprises an outer shaft, a multi-piece inner cutting core, and an aspiration and live suction tissue removal mechanism. Preferably, the outer shaft and the inner cutting core are composed of stainless steel or another suitable material that adds support and provides rigidity to the system to facilitate adequate waste flow for the removal of tissue and fluids. Stainless steel is a sufficient material for the cutting core and probe body, is less expensive than other materials, and as used in the present invention may provide performance advantages over expensive memory metals such as nitinol. The shaft of the atherectomy tool should be approximately 12" (12 inches) from handle to tip for the TUCP™ system and approximately 6" (6 inches) from handle to tip for the TPCP™ system. Preferably, the handle has an ergonomic design. The outer plastic handle houses the stainless steel cutting system.

The multi-piece inner cutting core should occupy approximately 80% of the total inner area spanned by a circumference of the atherectomy probe. The cutter should be slightly or partially recessed inside of the tip of the shaft so that it only engages tissue that has been directly inserted into the outer port. The design of the cutting core may resemble a pie with slices (i.e. two mirror-image slices) missing. The area occupied by the missing pie slices is preferably approximately 20% of the total inner area of the circle formed by a cross-section through the probe. Ultra sharp cutting blades are positioned on the edges adjacent the missing pie slices.

Figure 6:
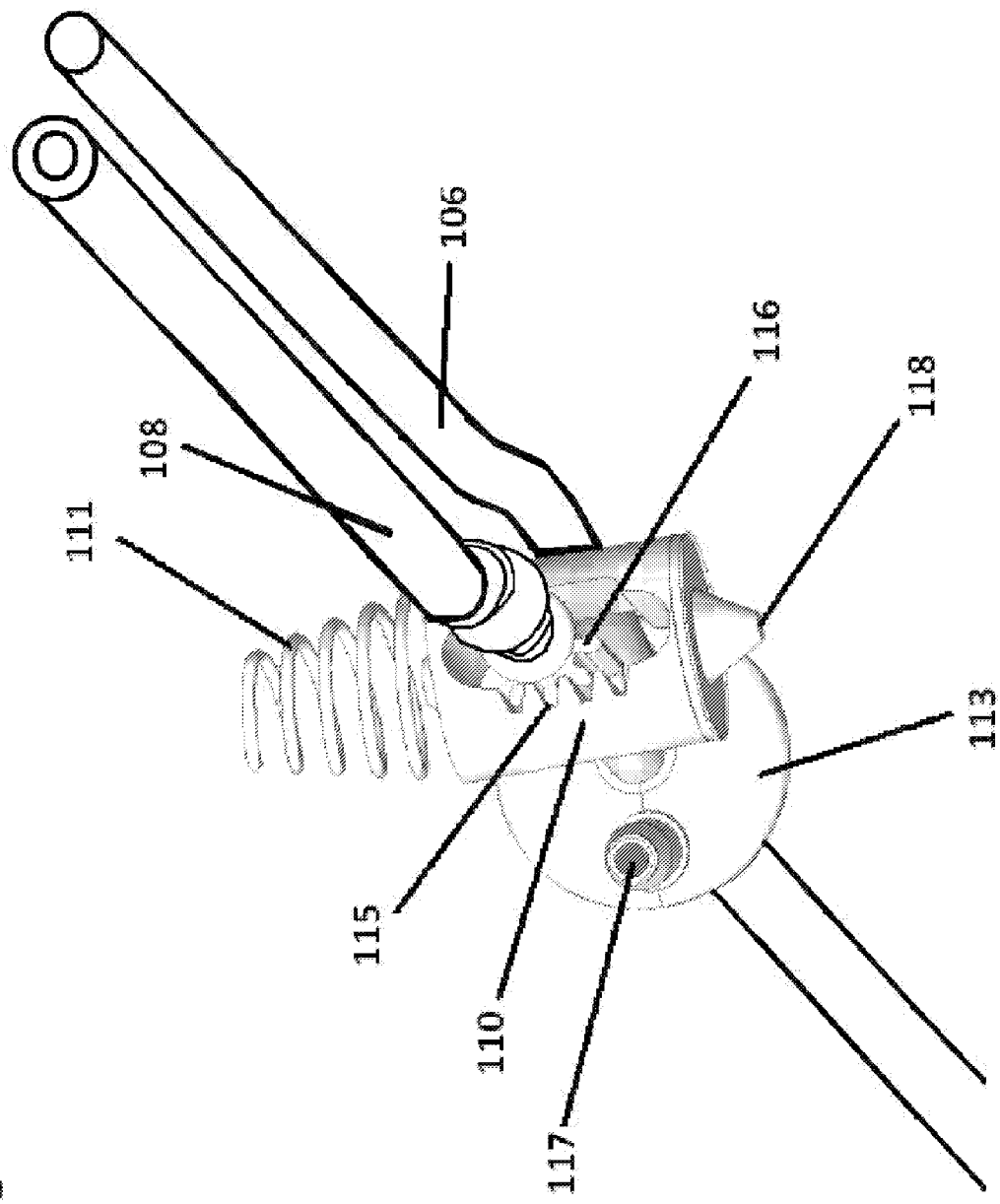
FIG. 6 highlights a select group of internal components without the outer handpiece as viewed from the proximal to the distal end, clearly showing the piston and spring actuation mechanism with the aspiration pipe passing through it, the fiber optic cable on the outside, and the base of the light cone with its connection port for the infusion pipe (not shown).
Figure 7:
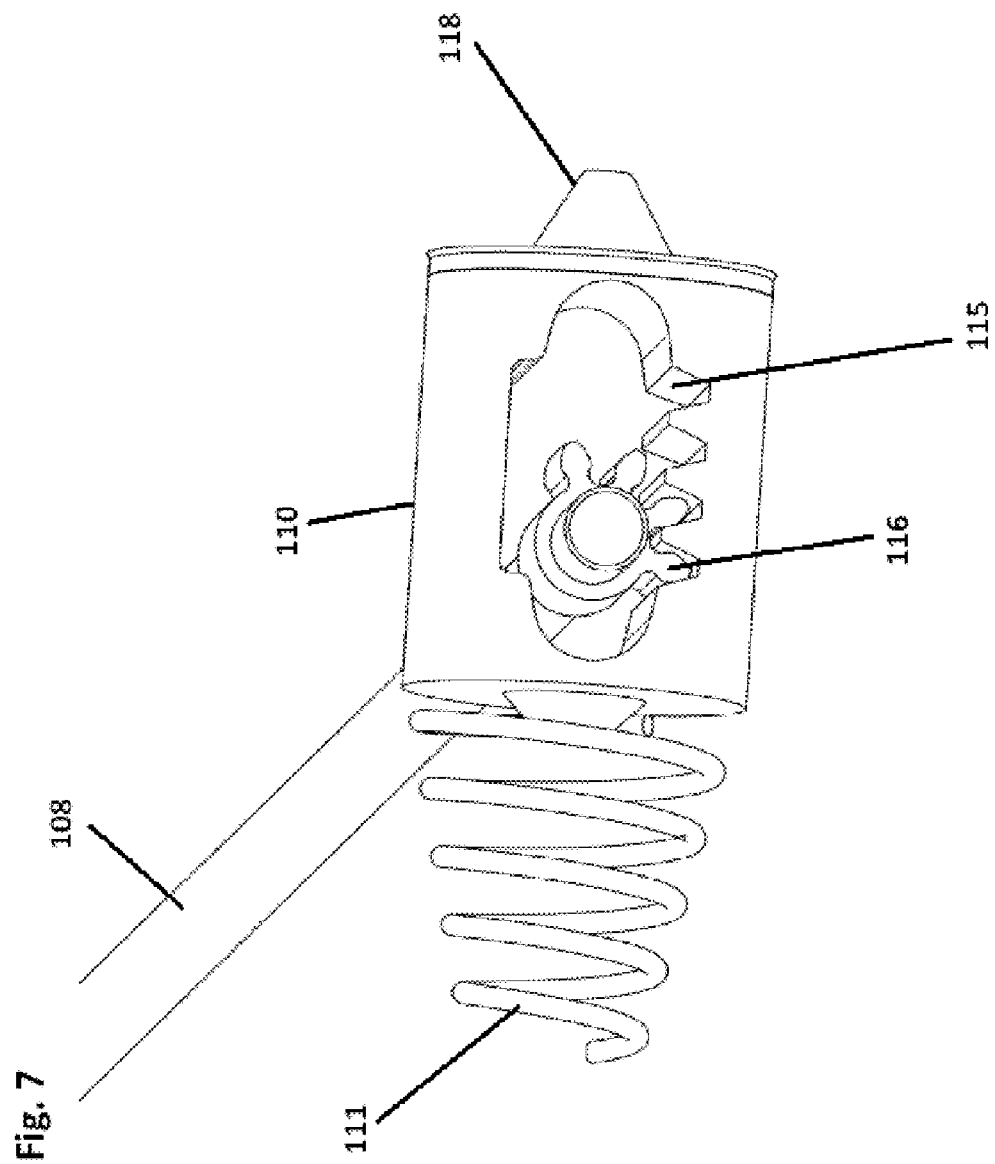
FIG. 7 highlights just the spring and piston, turned 90 degrees from in FIG. 6, with the aspiration pipe geared to the piston such that actuation of the piston through the lower stroke stop and spring drives the aspiration pipe and the cutter (not shown) at its distal end.
Figure 11:
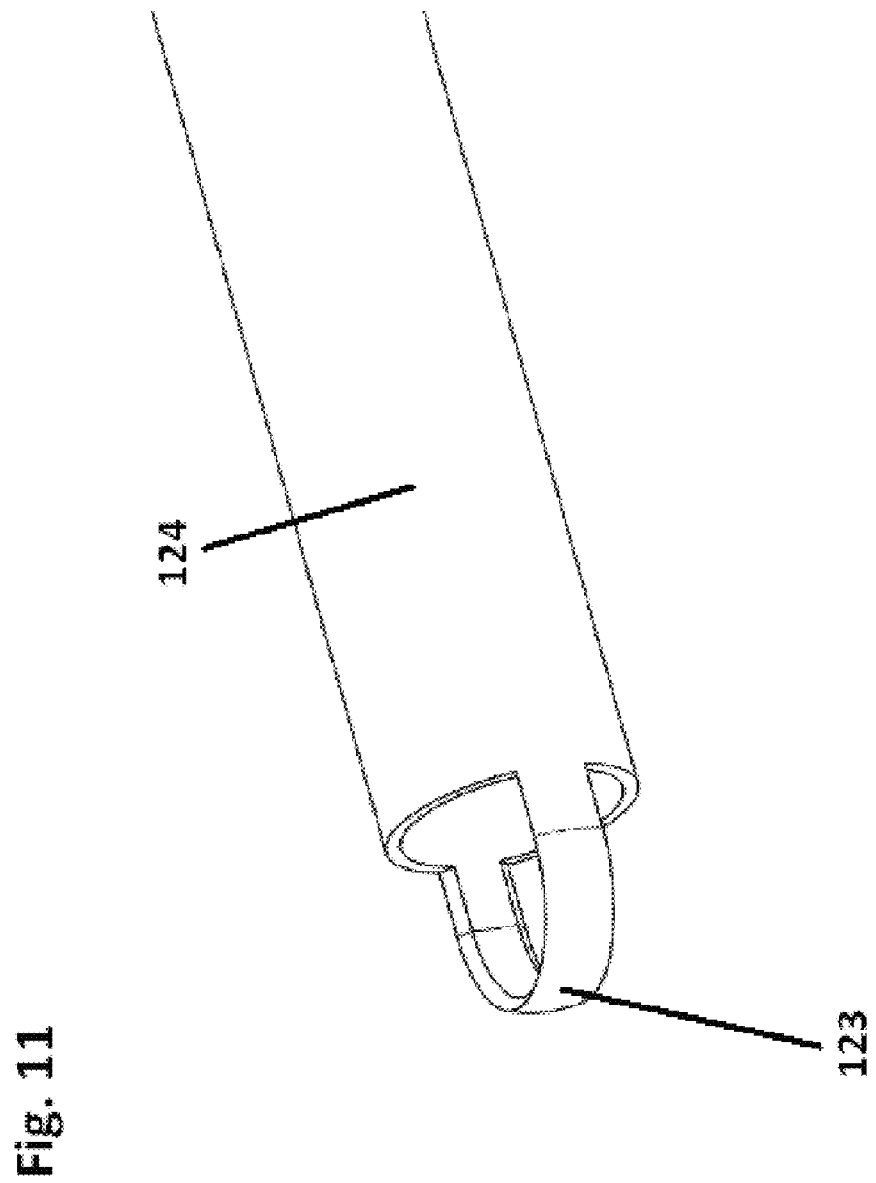
FIG. 11 shows only the blade, according to one embodiment in which it is an arch, connected to its cylindrical shaft which becomes the aspiration pipe at its proximal end and passes through and is geared to the piston for actuation to drive the blade's motion.

According to a preferred embodiment, as shown in FIG. 11 the cutter comprises a blade 123 and cylindrical tubular shaft 124 that turns into the aspiration pipe 108 towards its proximal end. The aspiration line 108 is shown in FIGS. 6-7 geared to the piston 110. Movement of the piston 110 actuates the gear 115/116 and turns the cutting core 124. Tissue severed by the cutting core 124 is easily suctioned out of the body since the aspiration pipe 108 and the blade 123 and cutting core 124 are integrated.

Preferably, the blades may be made of stainless steel. An internal driver is attached to the multi-piece inner core that spins it very rapidly at 15,000 rpm to 25,000 rpm. In a preferred embodiment, the internal driver spins the two-piece inner core at approximately 20,000 rpm. The reference art that includes heating elements to cut by cauterization (i.e. U.S. Pat. No. 5,571,130 cited above) teaches away from such high speeds because they are incompatible with heat transfer. The present invention does not rely upon heat transfer or cauterization and therefore blade speed is not limited. Higher speeds than those of the reference art are advantageous and complementary to live aspiration or continuous vacuum suction. The higher speeds produce smaller (and more frequently cut) tissue fragments to avoid blockage or kinking in the removal line as from large fragments produced by less frequently cutting slower blade motion. The torque to move the cutter (i.e. via rotation, reciprocation, or slicing movement) can be driven either pneumatically (i.e. via compressed nitrogen or air) or by an electric motor powered by the surgical console. The handpiece power cord for the cutting core driver is unique from other power cords such that its presence is sensed by an identification sensor on the console.

An average prostate size for those with BPH seeking surgical intervention is around 60 grams. It is expected that de-bulking a core of 20 grams (around one-third of the prostate) should provide sufficient patient satisfaction. Thus, the mechanical coring operation should be continued until a mass of approximately 20 grams has been removed. However, as every individual case is different the physician's best judgment should be used to instruct when to stop cutting and in some cases more or less than this amount will be removed to provide adequate relief.

Figure 2:
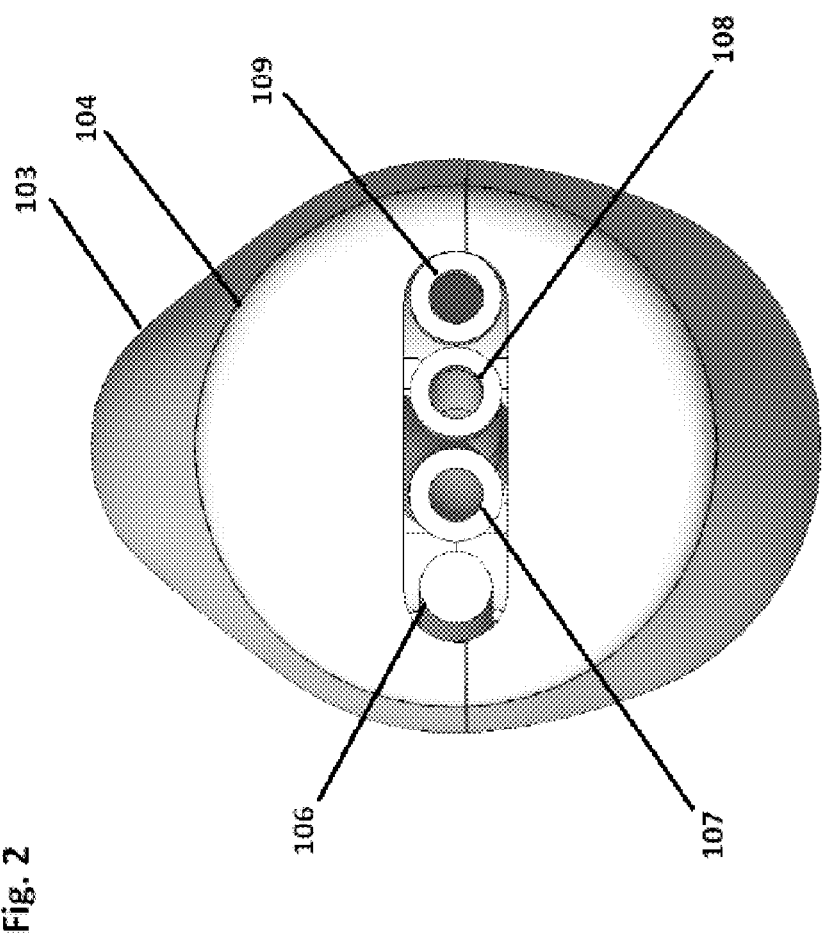
FIG. 2 shows a vertical cross-sectional view through the coring probe of FIG. 1 illustrating the four functional pipes, each for performing a different function, and how the top of the instrument may be tapered for improved ergonomic handling.
Figure 3:
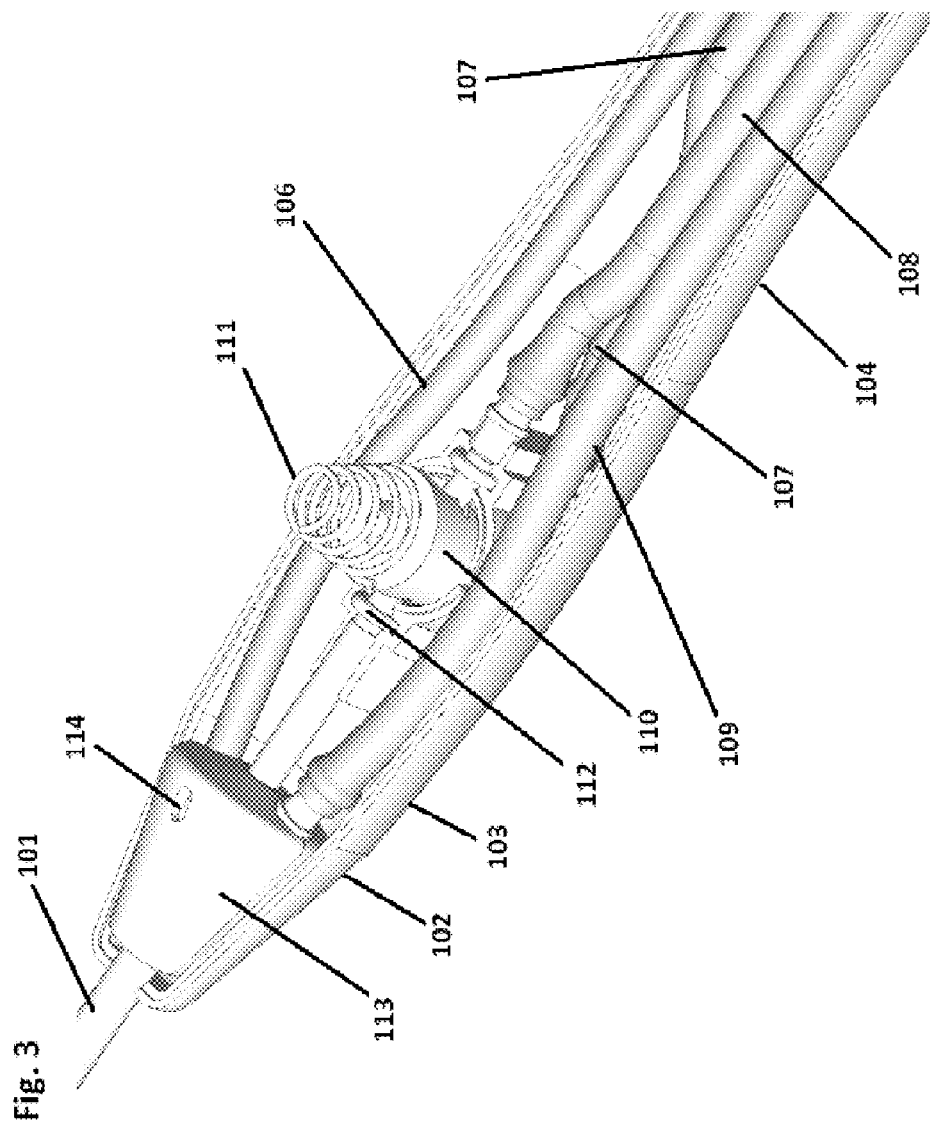
FIG. 3 shows a horizontal cross-sectional view along the longitudinal central axis of the probe from the left side illustrating how various elements including the functional pipes, the light cone, and the spring and piston actuation mechanism fit together compactly within the proximal shaft and handpiece.
Figure 4:
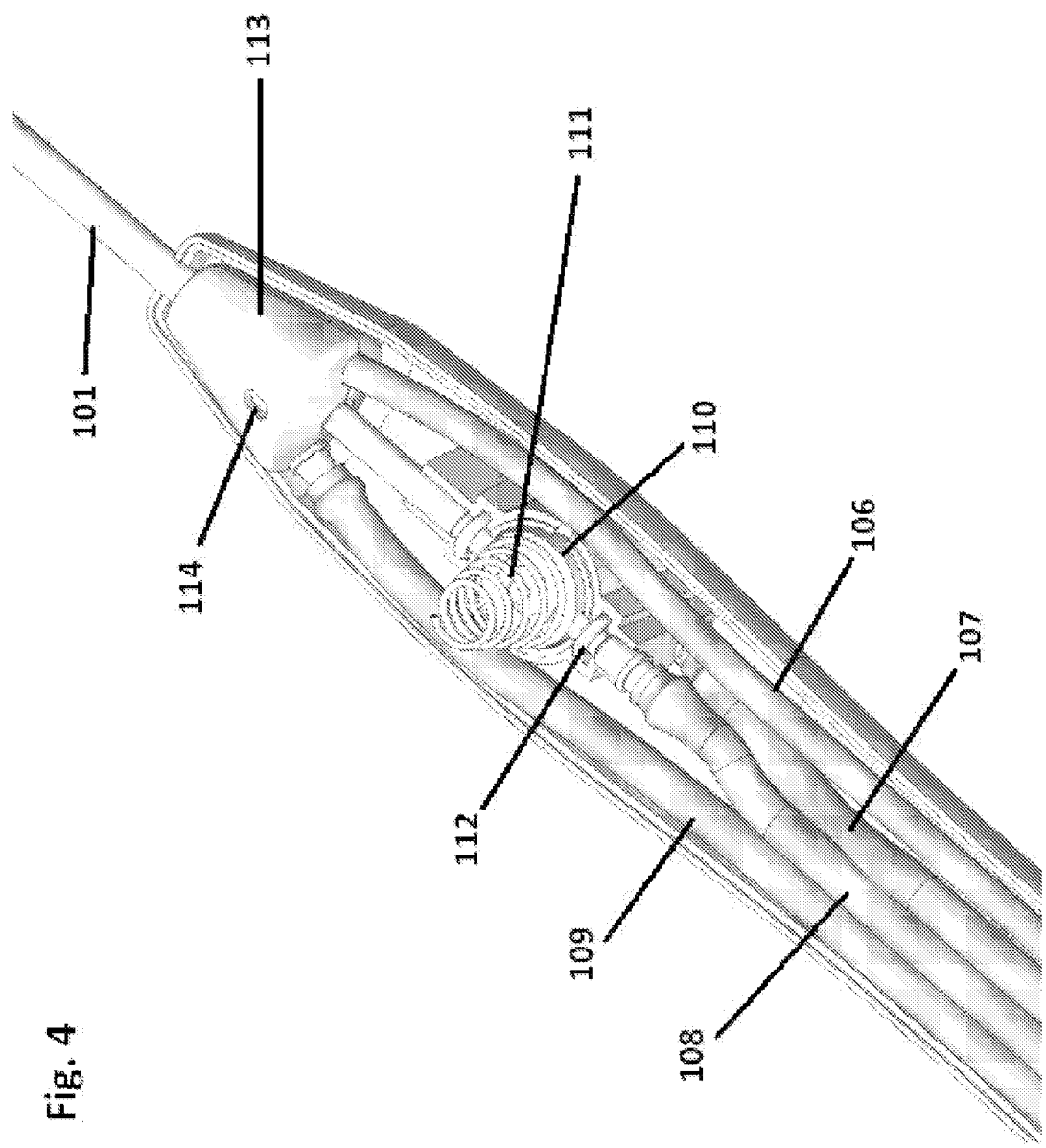
FIG. 4 shows a similar horizontal cross-sectional view as in FIG. 3 but looking from the right side and better illustrating how the two central pipes, the aspiration pipe above and the power supply pipe below, connect with the piston actuation mechanism.

Four or more pipes, collectively 105 as shown in FIG. 1, extend through the proximal end of the instrument and extend distally to different lengths as necessary. The pipes may be arranged side by side when viewed from a cross-section through the instrument as shown in FIG. 2. According to a preferred embodiment, the pipes are arranged left to right as follows as shown in FIGS. 3-4: infusion pipe 109, aspiration pipe 108, power supply pipe 107 (i.e. a pneumatic air source according to a preferred embodiment), and means for visualizing 106 (i.e. a fiber optic cable).

The aspiration pipe 108, as shown in FIGS. 2-7, 13, and 15, is one of four or more pipes (collectively 105 as in FIG. 1). In the embodiment in which the cutting core is shaped like a solid cylinder with pie slices missing the aspiration volume is approximately 20% of the cross sectional area of the atherectomy probe left vacant by the inner cutting core. The function of the aspiration system is to facilitate the removal of excised tissue from the internal surgical site to an external self sealed biohazard waste cassette and bag attached to the surgical console via vacuum suction and irrigation. Aspiration is activated when a luer lock connector attaches to a unique cassette on an identification-sensing surgical console. The aspiration line tubing should be transparent and also include measurements (i.e. cubic centimeters ($cm^3$ or cc's)) so that the flow of materials, including fluids and tissue, can be easily monitored and analyzed. Transparent tubing also permits general flow characteristics to be observed so that kinks, bubbles, jams, etc. can be promptly noted and remedied.

Following the removal of sufficient amounts of core prostatic tissue, the site should be sealed to ensure and maintain hemostasis. Any sealing system and method known in the art is appropriate including: tamponading balloons, cauterizing probes, and topical adhesives (i.e. gels, powders, patches, plugs, etc. that can be sprayed, inserted, plugged, injected, adhered, etc. including thrombins, fibrins, fibrin glues, gelatins, platelets, etc. derived from human, bovine, porcine, synthetic, etc. sources). A preferred sealing system and method is the cooling dual tamponade prosta plasty system described herein and also in commonly owned, co-pending U.S. Provisional Patent Application No. 61/048,427 (entitled "Benign prostatic hyperplasia surgical intervention system", filed Apr. 28, 2008) of which the benefit is claimed and which is herein incorporated by reference to the extent it is not inconsistent with this application.

The controlled access methods (i.e. micropuncture, progressive dilation) and selective removal of core hyperplastic prostate tissue using the mechanical coring techniques described herein provide the ability to relieve stricture at the bladder neck without impairing functioning of the surrounding musculature. The urethral lining bladders and internal and external sphincter muscles are left intact while the core prostate is accessed and de-bulked including by the elimination of excess tissue at the bladder neck and while preserving the prostatic capsule. Normal functioning of the urethral musculature is important because the regular contract and release cycles are responsible for a healthy ejaculatory response and for bladder continence and control. The internal sphincter is responsible for involuntary muscles that control the ejaculatory response. The external sphincter is responsible for voluntary muscles that control the bladder and the ability to urinate. Damage to the musculature could cause problems such as dry climax, reverse ejaculation, incontinence, and bladder control issues. The present invention quickly sculpts the prostate to relieve constriction without damaging musculature or the basic capsular shape. The load on the musculature is restored to normal sustainable levels that save the muscles from the overuse that occurs during BPH to compensate for the increased pressures caused by hyperplastic tissue imposing upon natural lumens.

Destruction of the natural urethral lining and/or musculature from other more aggressive, non-selective (i.e. capsule cutting/destroying, urethral lining irritating, and collateral damage to healthy tissue) BPH treatment procedures can take weeks or even months to heal. This healing process is especially slow and problematic in individuals with diabetes, peripheral vascular disease, and others with compromised circulatory and/or immune response. The non-destructive transperineal core prostatectomy (TPCP™) and the transurethral core prostectomy (TUCP™) devices and procedures described herein would be especially helpful to these individuals that may otherwise be poor candidates for other contemporary surgical methods. Contemporary BPH surgical methods (including laser, microwave, etc. with their accompanying collateral damage) could create complications in these at-risk individuals from their inability to heal fast enough. On the other hand, leaving at-risk patients untreated results in their further muscular deterioration from muscle exhaustion and inability to overcome high stricture pressures. The present invention may be the only option for these patients that solves the stricture problem without creating more problems taking into account their reduced capacities for healing and regeneration. The technology at this early stage also looks like an excellent option to treat BPH at much earlier progressive disease state than current surgical techniques since the trauma and side effects appear to be significantly reduced or eliminated when used as indicated in otherwise healthy patients.

Another key feature of the invention is the unique identification sensitive surgical cassette or card that is inserted into the console to determine the product being used. This cassette connects to the surgical console and is essential to associate the console controls with the disposable surgical instruments. For example, U.S. Pat. No. 6,902,542 by Raphael Gordon and assigned to Alcon, Inc. discloses an "Identification System for a Surgical Cassette" comprising a series of tabs that are variably opaque to translucent in a pattern unique to a particular cassette. The use of an identification system supports and maintains FDA mandates on product tracking and ensures that a product is not re-used. Reusing a product could reduce performance and result in patient injury or infection due to biohazardous, bloodbourne pathogens and material contaminants. Such pathogens and contaminants would be extremely difficult, if not impossible, to clean and sterilize due to the nature of the small diameter plastic closed/sealed cassette system. However, with disposable products it is also important to protect healthcare providers and others who come in contact with disposed biohazardous materials. Thus, a sealed biohazardous containment system has been designed for disposal. The ID-sensing mechanism provides a secure way to ensure hygienic instruments while removing the cleaning obstacle and risk of inadequate sterilization.

The identifying cassette/card and identification-sensing console system of the present invention is distinguishable from that of U.S. Pat. No. '542 and easier to use. In one embodiment, the cassette of the present invention comprises a unique pattern of insulating regions within a conducting material placed in between two other conductive materials. The insulating regions may be composed of air gaps (i.e. a hole-punch pattern) or discrete sections of insulating materials having a dielectric constant (permittivity) higher than that of the surrounding conducting material. Within the console, an electric sensor on one side of the cassette recognizes the cassette that is the "key" according to the conductivity pattern it creates as measured by, for example, a reduced current in certain regions.

The cassette also has exposed tubing set(s) that allows for pinch valves to actuate against the tubing lines to eliminate residual/built up aspiration in the lines of the atherectomy probe and work with the linear aspiration controlled by the operator. The pinch valves are unique because they are the only way to reduce/minimize/eliminate aspiration to reach 0 (zero) mmHg (millimeters of Mercury) aspiration when the operator so chooses to provide a significant performance/safety advantage. Pinch valves provide a way to take control of built up aspiration that may accidentally encarcerate itself into the cutters port. With pinch valves the tissue can be released from the cutters port without destroying it.

Alternatively, an encoded surgical identification card similar to a credit or gift card may be used. The card tells the console system what product is being used with lot numbers, etc. Preferably, such a card is encoded for only one use and after being used once becomes permanently deactivated. To use the console again a new card is required. A new card is provided with each new disposable product purchase (i.e. in the sterile surgical pack that has the disposable atherectomy probe in it). The surgical console requires a new disposable card with each use and the codes embedded within the card are encrypted data that cannot be hacked.

The surgical console serves as an operations control center for the entire surgical system. This console is smaller than those of conventional BPH treatment systems because no large energy generating unit is required. The console of the present invention can simply plug into conventional wall electrical outlets and use this electrical energy as a source for the atherectomy probe driver and other controls. Optionally, back-up batteries can be provided for use with the system in the event of an external electrical power outage or brown-out during surgery.

The atherectomy probe cutting core rotation speed can be controlled by either an electric drive handpiece on an ergonomic handle or a foot treadle. Both the handle control and the foot treadle control connect to the console. The console display visibly shows the atherectomy speed in RPM (revolutions per minute), CPM (Cuts Per Minute) and as a percentage of maximum capacity. The console also features a third overriding means to control the atherectomy driver speed along with an emergency stop switch. All rotation speed controls for the atherectomy probe cutting core enable the operator to obtain a range of fixed speeds and to adjust the speed. The driver shaft includes plastic components and should not be flashed or sterilized for reuse as it would be impossible to verify sterility and cleanliness of micro internal components for multi patient use. The atherectomy probe is connected to the console by a first quick connect relay which connects the driver and a second quick connect relay which connects the aspiration line to the sealed single use, disposable, biohazard collection cassette.

Illumination within the light pipe is also controlled through the console. The console houses a metal halide, light emitting diode (L.E.D.), or xenon light source of at least two bulbs so that a back-up is readily available in the event one bulb burns out. The console light source compartment provides ventilation for the bulbs to dissipate and prevent heat build-up. The light source compartment of the console can be easily accessed at the conclusion of the procedure and allows easy maintenance and exchange of bulbs without interfering with the other displays and instrumentation controls on the console.

Preferably, a light is built into the probe body. This light can be powered by and have its source in the console or independently within the probe handpiece or shaft. The probe light should be capable of visualizing the probe tip to operate in coordination with a urethral camera. Together the urethral camera and probe light focused on the tip can track the location of the probe in sub tissue below the camera and evaluate the progress of the procedure, including its relief to the target stricture, in "real time". This feedback enhances efficiency by allowing instrument positions to be adjusted promptly as needed and enabling the full amount of coring to be achieved before instruments are withdrawn so that they don't have to be reinserted to finish the job.

The console also has a docking station for the surgical cassette. Through an identification sensing mechanism, the console detects the cassette/card to activate the peristaltic pump which engages the aspiration tubing lines of the cassette. The cassette has two aspiration lines attached to the pump to provide a back-up in the event one line becomes clogged or kinked. All aspiration and pump lines are fitted with luer locks for quick and easy assembly and detachment.

Any commercially available medical facility endoscopic camera and monitor system can be attached to the console via a quick connect port and the use of adaptors.

The console screen displays all control variables in well-lit, large, easy-to-understand symbols. Up and down arrow control buttons are provided for adjusting: the illumination, the atherectomy probe cutting core driver rotation speed, and the aspiration rate via the vacuum suction from the console's internal peristaltic pump. A second internal peristaltic pump could also be used to control coolant infusion speeds based upon foot pedal position or console adjustment controls.

A review of the illustrations and identification of the reference numerals follows.

FIG. 1 shows the entire mechanical coring atherectomy probe of the present invention looking from the proximal (at lower right) towards the distal end (at upper left). At the distal end is the cutting shaft covered with a thin, tightly-wrapped, opaque cover 101. Underneath the cover 101 is the light sheath 125 which surrounds the cutting core 124, the cutting core 124 becoming a blade 123 distally and an aspiration pipe 108 proximally. Proximal to the opaque cover 101 is a first and distal tapered portion of the handpiece 102 that encompasses the light cone 113, followed by a second intermediate curved portion of the handpiece 103 that encompasses the piston 110 and spring 111 actuation mechanism, followed by a third proximal straight portion of the handpiece 104 that encompasses an assortment of functional pipes 105.

FIG. 2 shows a cross-section through the third portion of the handpiece 104 illustrating how four functional pipes (105 collectively) may fit together in a linear array and how the periphery of the second portion of the handpiece 103 has a variable size and shape for improved ergonomic handling, a better fit of the internal components (i.e. actuation mechanism) it holds, and a smoother interaction with body tissue in the event it is necessary to insert the instrument deeply enough that portion 103 actually enters the body. Any number of functional pipes 105 having any number of functions can be provided so long as the pipes fit neatly together within the housing and are securely sealed and insulated to prevent leakage or safety issues. The pipes 105 need not be arranged linearly but could also be staggered, arranged in a cross, arranged in a circle, etc. According to a preferred embodiment there are four pipes which include (from left to right in FIG. 2): (i) a fiber optic cable or other means for visualizing 106 (including a source of recording such as a camera and/or a source of illumination such as a light); (ii) a power source 107 (i.e. a pneumatic air supply that feeds a piston 110); (iii) an aspiration line 108 removing tissue that turns into the cutting blade 123 distally and is geared to an actuation means (i.e. a piston 110); and an irrigating infusion line 109 that delivers coolants, nutrients, therapeutic agents, and/or water to flush and cleanse the coring site, draining distally through openings 119 in the light sheath 125 and cover 101.

The infusion pipe carries an infusate. The "infusate" referred to herein simply means any infused material including gases, liquids, and solids or mixed state dispersions. The infusate could be any number of materials including water, a refrigerated saline solution, or these materials including an antiseptic, anti-inflammatory, antibiotic, analgesic, or other therapeutic agent dissolved or dispersed therein.

Figure 5:
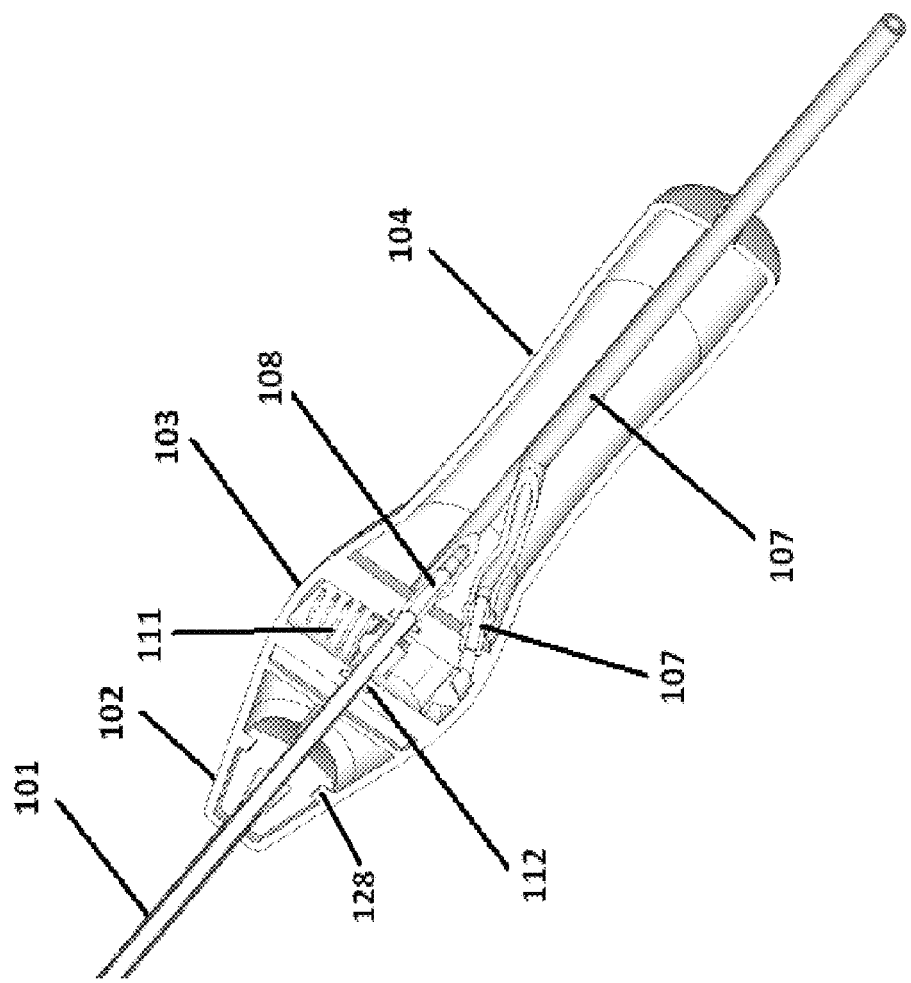
FIG. 5 shows another horizontal cross-sectional view along the longitudinal central axis in which the instrument has been turned approximately 90 degrees from the view in FIG. 3 or FIG. 4 to fully show the spring and piston from bottom to top with the power supply pipe obscuring the aspiration pipe at the proximal end.

FIGS. 3-5 show how the internal components fit together within the first 102, second 103, and third 104 portions of the handpiece. The light cone 113 contains one or more indentations 114 that serve as a key hold for one or more corresponding protruding notches 128 on the inside of the handpiece. The indentation 114 is shown in FIGS. 3-4 with the notch 128 shown in FIG. 5. Three of the pipes including the infusion pipe 109, the aspiration pipe 108, and the fiber optic cable or light pipe 106 (left to right in FIGS. 3-4) connect to and enter the light cone 113. The power supply pipe 107 does not enter the light cone but terminates at the piston 110 to provide air pressure or another means for driving the piston 110. A spring 111 on one side of the piston 110 provides the return force and a stroke stop 118 (see FIGS. 6-7) on the other side of the piston 110 maintains a space below/beside the piston face for the air pressure to work properly to be able to drive the piston.

The aspiration pipe 108 passes through the center of the piston 110 and is maintained in position by a means for stabilizing such as the distal and proximal O-rings 112. It is helpful for the aspiration pipe 108 to be stabilized in some manner since the pipe 108 turns into the cutting core 124 and blade 123 at the instrument's distal working end. If the aspiration pipe 108 is not properly stabilized damage may result due to imprecision while the blade 123 interacts with tissue. The aspiration pipe 108 continues on to enter the light cone 113 through the base of the cone and to exit through the top of the cone where the aspiration pipe 108 becomes the cutting core 124 is surrounded by the light sheath 125 and its opaque cover 101.

FIG. 5 shows how the handpiece can be segmented with the first portion 102 (containing the light cone 113) divided from the second portion 103 (containing the actuation means) and the third portion 104. FIG. 5 also better illustrates how the power supply pipe 107 bends and passes low into a chamber in the second portion 103 to feed the piston 110. The aspiration pipe 108 does not connect to the power supply pipe 107 proximally (as it may appear at first glance) but rather, from the angle shown the power supply pipe 107 is directly over and obscuring the aspiration pipe 108 underneath it at the proximal end.

Figure 10:
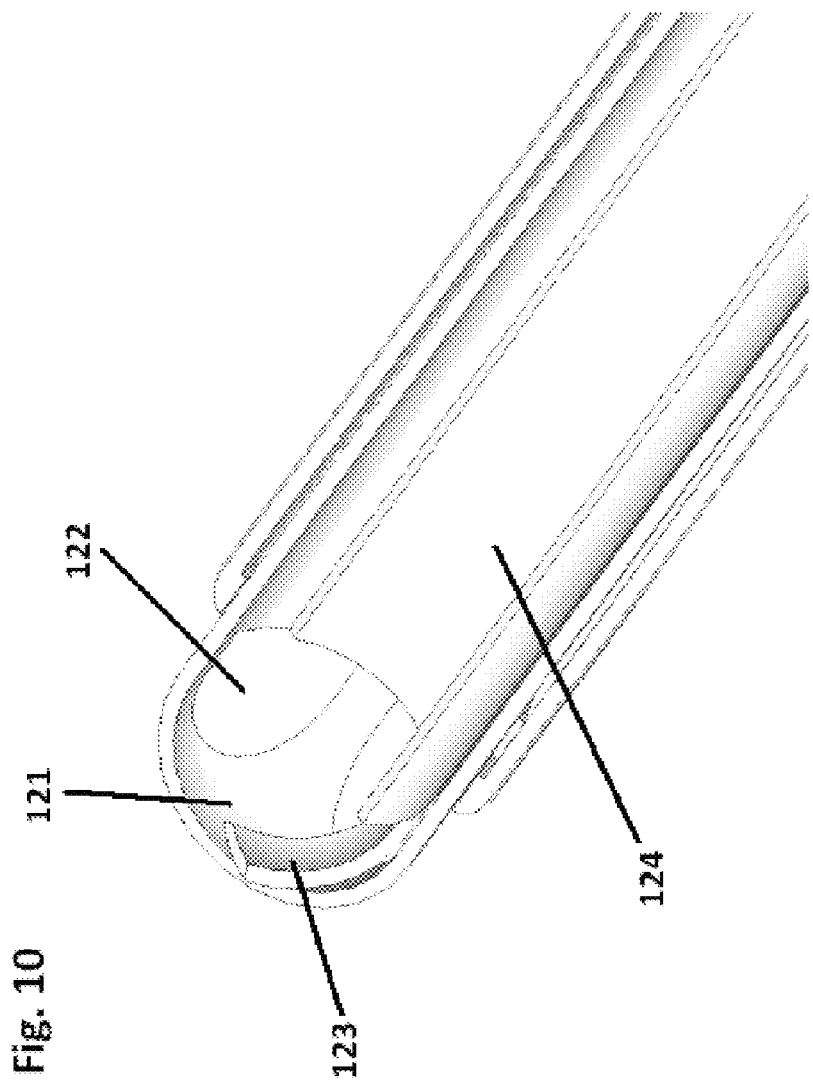
FIG. 10 shows a cross-section cutout view of the distal end of the instrument highlighting how the domed hood fits within the light sheath and how the blade (with a portion chopped off) fits within the domed hood with the shape of the blade complementing the geometry of the hood.

FIG. 6 shows just two of the pipes, the aspiration pipe 108 and fiber optic cable 106 to more clearly show how the aspiration pipe 108 is geared to the piston 110 with protruding extensions 116 on a wheel surrounding the pipe mating with corresponding grooves 115 within the piston 110 such that movement of the piston 110 turns the wheel and moves the pipe 108 and the cutting core 124 on its distal end (see FIGS. 10-11). FIG. 6 also shows a connector valve 117 through the base of the light cone 113 for the infusion pipe 109 to deliver infusate to a chamber 127 (see FIG. 13) in the light cone 113 for feeding the light sheath 125.

FIG. 7 more clearly shows just the aspiration pipe 108 and its interaction with the piston 110 and spring 111.

Figure 8:
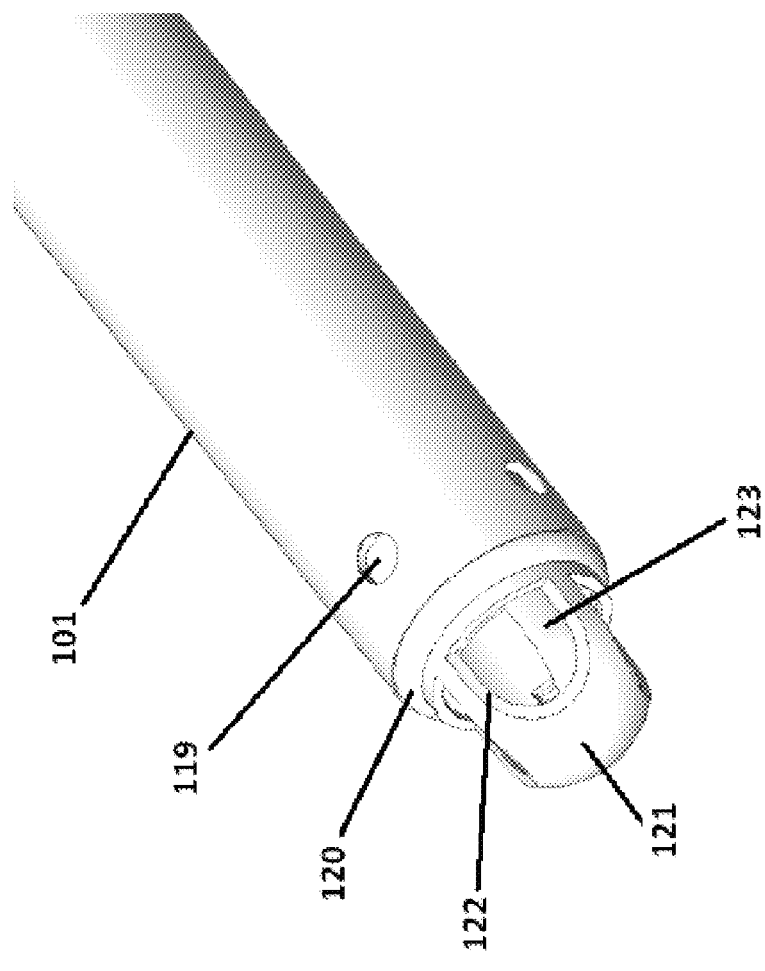
FIG. 8 shows the distal cutting end of the mechanical coring atherectomy probe with the blade housed within the dome-shaped hood and the ports through the light sheath and its opaque shrink-wrapped cover to vent the infusate.
Figure 9:
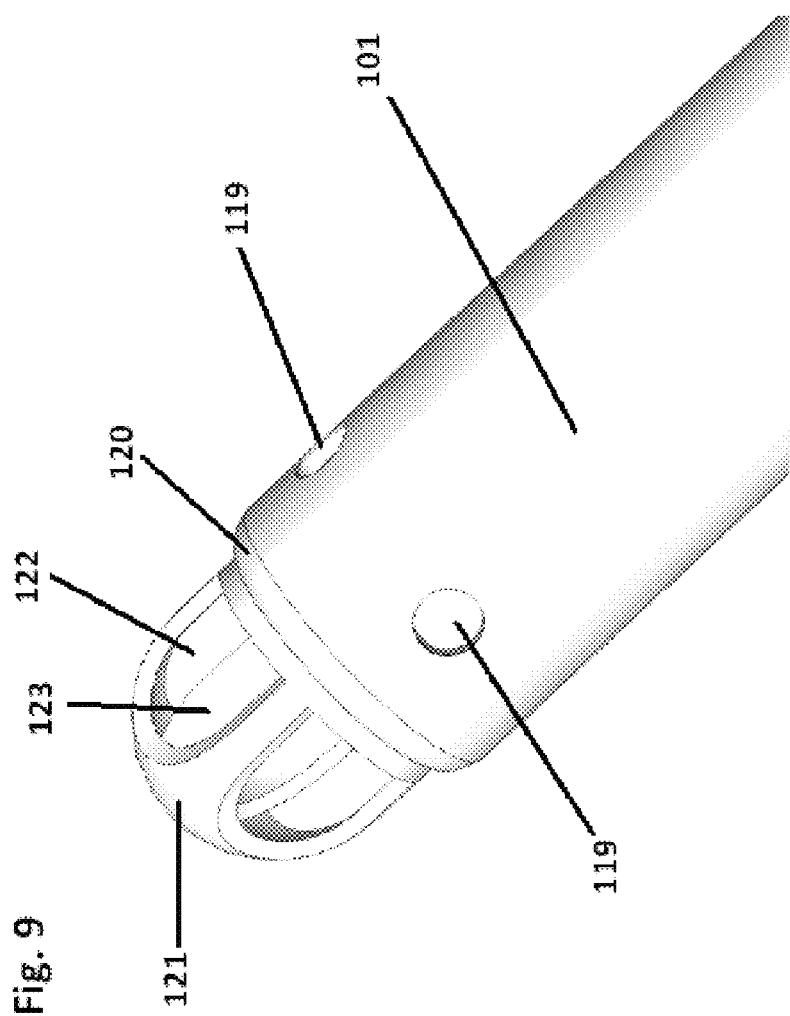
FIG. 9 shows the distal cutting end of the probe, as in FIG. 8, from another perspective better illustrating how the blade fits within the domed hood and how the lens portion at the distal end of the instrument tapers slightly approaching the hood.

FIGS. 8-12 show the cutting components at the distal end of the instrument. FIGS. 8-9 show the cutting blade 123 within the protective hood or dome 121 and the windows 122 therein through which the blade 123 engages with tissue. There is a lens 120 at the distal end of the light sheath 125 (125 as shown in FIGS. 13-16) and holes 119 extending through both the light sheath 125 and its opaque cover 101 for venting the infusate which is conveyed through the extruded grooves 126 in the light sheath 125 (see FIGS. 13-16).

FIGS. 10-11 show how the distal blade 123 is connected to a cutting core 124. The cutting core 124 extends along the shaft and eventually turns into the aspiration pipe 108. FIG. 10 also shows how the curvature and geometry of the blade 123 can be designed to correspond to the curvature and geometry of the protective hooded dome 121 to cleanly slice tissue through the windows 122 upon impact.

Figure 12:
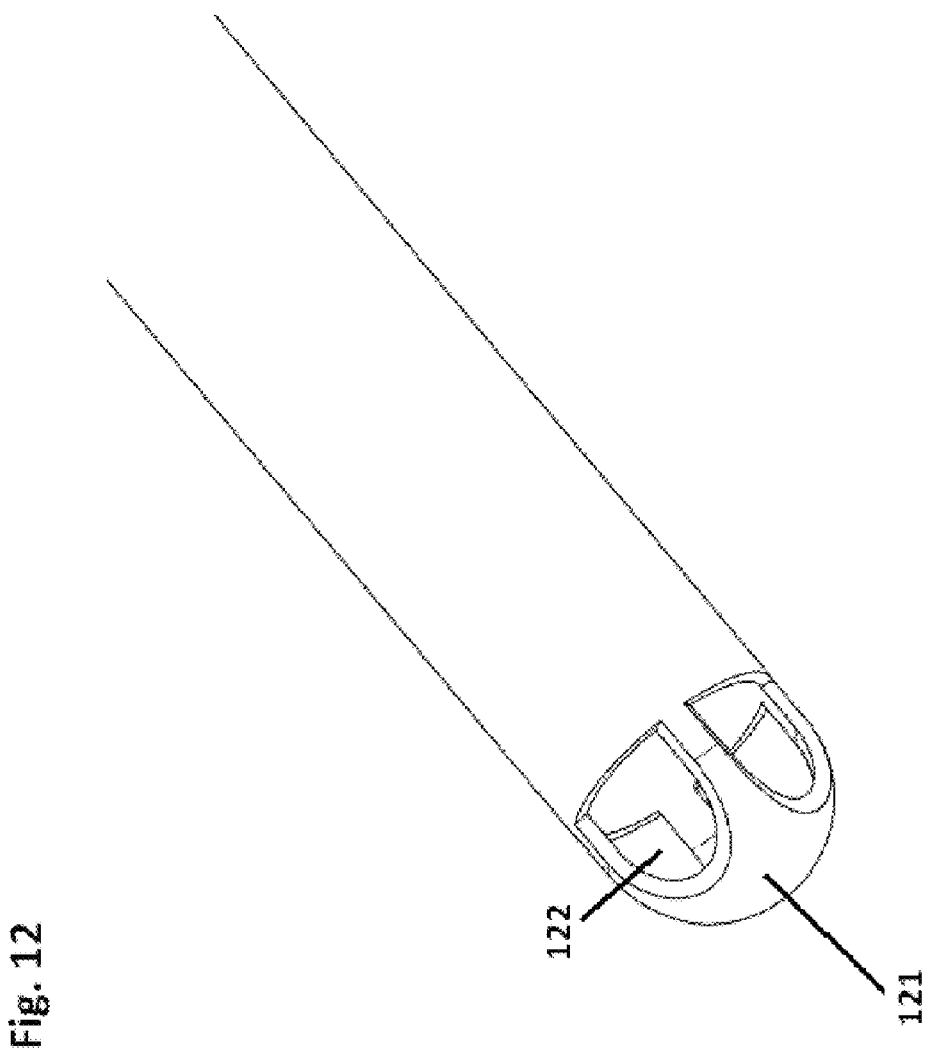
FIG. 12 shows only the domed hood or cover for the blade with various openings/portals/windows therein through which the blade interacts with and severs tissue.

FIG. 11 shows only the blade 123 and its integrated cutting core 124 without the dome 121 while FIG. 12 shows only the hooded dome 121 and its cut-out windows 122 therein without the blade 123.

Figure 13:
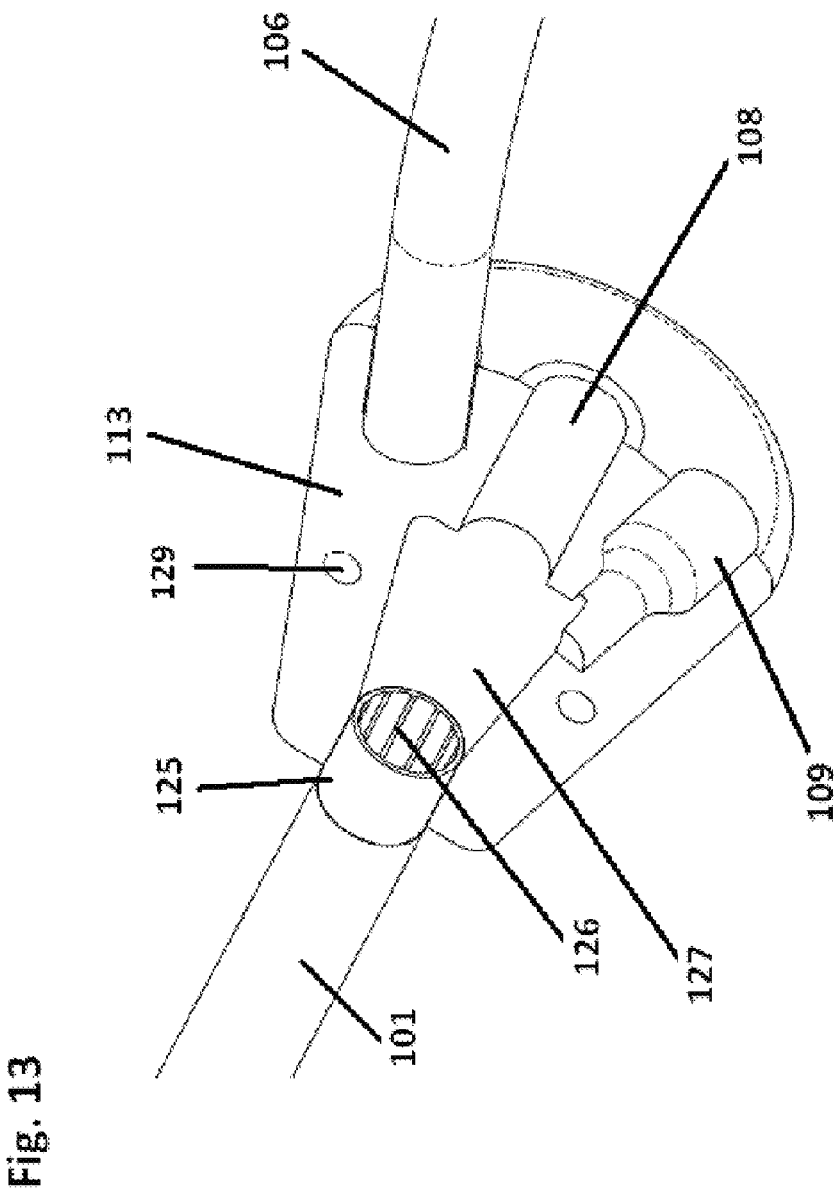
FIG. 13 shows a cross-section through the light cone, with the fiber optic cable or other visualization means leading into it on the right side, and the covered light sheath with extruded grooves therein (for conveying infusant) leading out of its tapered tip at the upperleft.

FIG. 13 shows how various ports connect within the light cone 113 including how the aspiration pipe port 108 and infusion pipe port 109 connect to a central chamber 127. Through the central chamber 127 infusate is delivered distally to the target cutting zone (to exit through distal ports 119 as in FIG. 16) and severed tissue is suctioned proximally out of the device to be removed from the body. Infusate is conveyed by the light sheath 125 through extruded channels or grooves 126 therein. One half of the light cone 113 may contain holes 129 therein for connecting with protrusions in the other half.

A fiber optic cable 106 or other visualization means feeding the light cone 113 provides light to the target cutting zone at the distal end of the instrument through the light sheath 125 that forms the periphery of the cutting core 124 in the distal region. An opaque cover 101 outside of the light sheath 125 prevents light from the fiber optic cable 106 from dissipating through the transparent sheath 125 so that the light actually reaches the distal end of the instrument to be concentrated and focused onto the cutting elements (123, 122, 121) by the lens 120 at the distal end of the light sheath 125.

Figure 14:
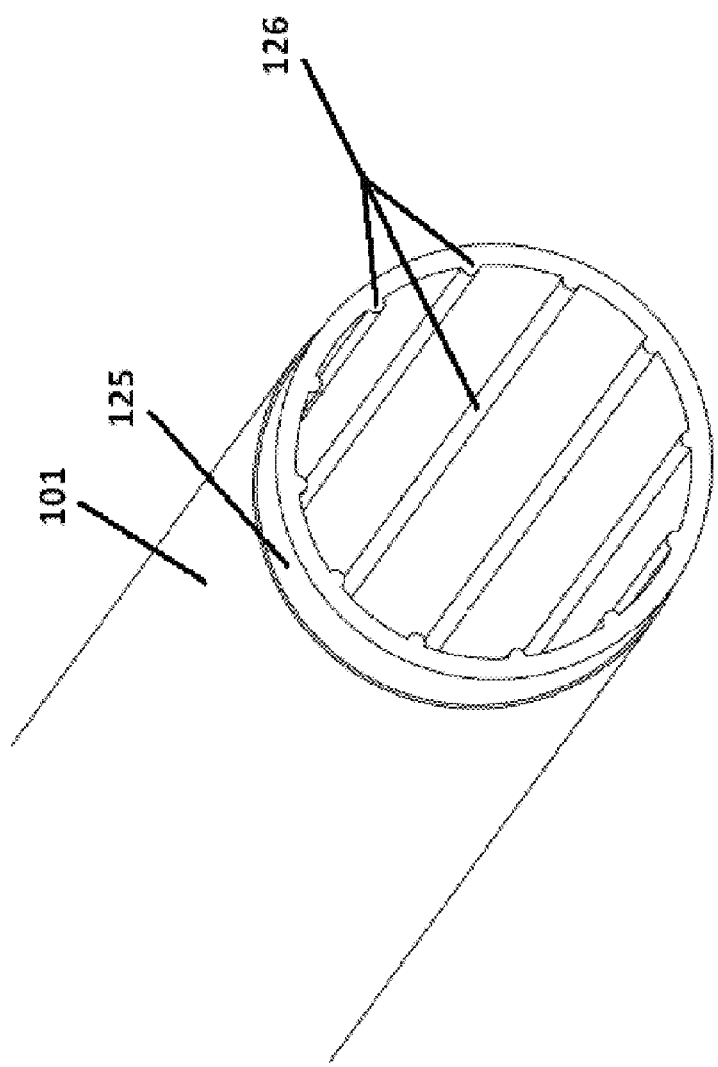
FIG. 14 shows the light sheath with extruded grooves therein for conveying infusant and a thin opaque cover on its outside for preventing the escape of light.

FIG. 14 shows how the thin opaque cover 101 wraps around the light sheath 125 and how the sheath 125 is capable of conveying infusate with the extruded grooves 126 therein.

Figure 15:
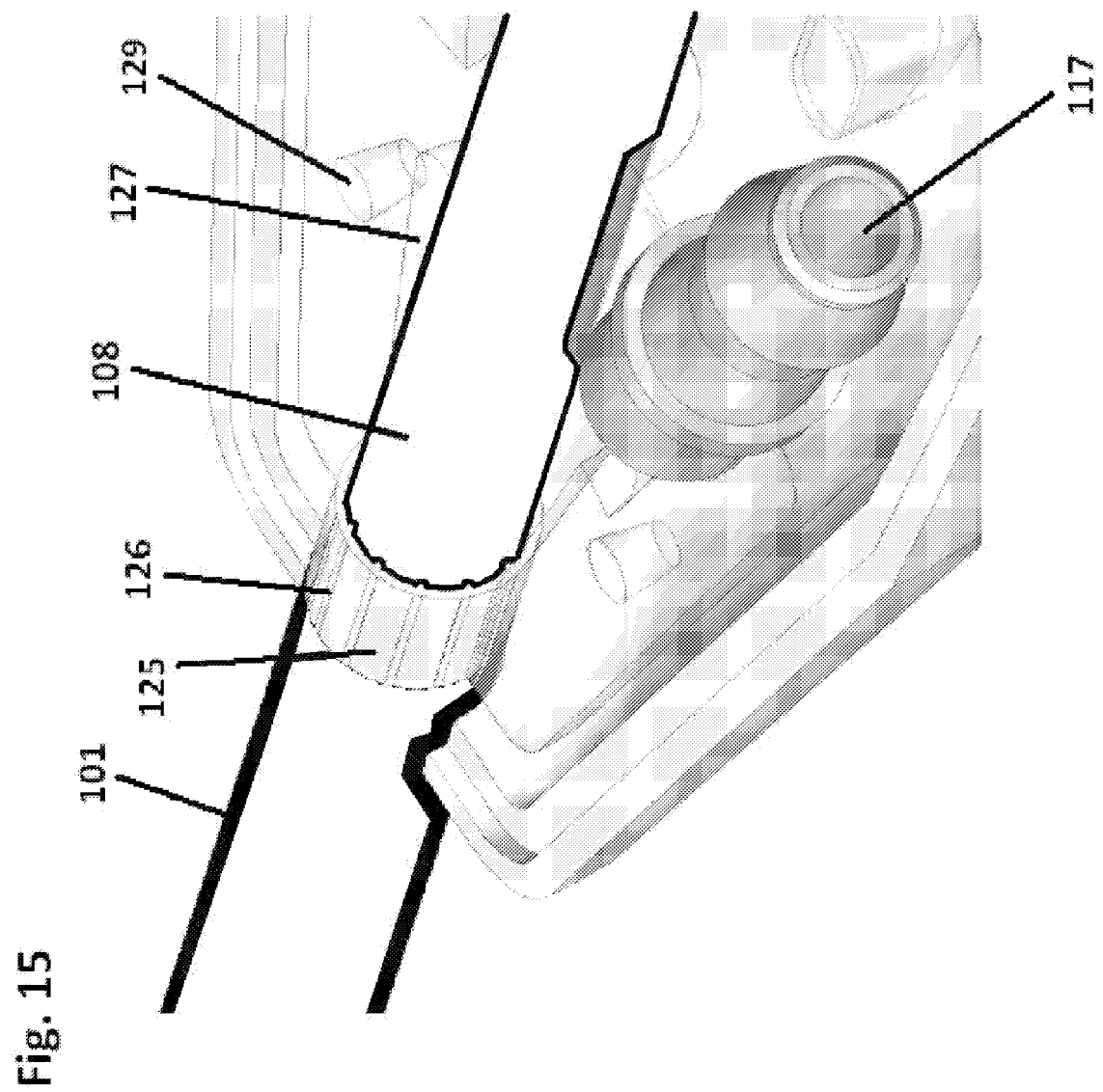
FIG. 15 shows a close-up view of how a central chamber within the light cone is feed by an infusion port at the lower right and in turn feeds the covered light sheath at the upper left.

FIG. 15 shows how the elements of FIG. 14 connect with the light cone 113 and how the light sheath 125 turns into the aspiration pipe 108 within the light cone 113. The light sheath 125 begins covering the aspiration pipe 108 in the light cone 113 and is not needed over the aspiration pipe 108 at the proximal end of the instrument. FIG. 15 also shows how the connector valve 117 for the infusion pipe 109 feeds the chamber 127 and the grooves 126 in the light sheath 125.

FIG. 16 more clearly shows how the light sheath 125 turns into a lens 120 at its distal end and how the holes 119 through the light sheath 125 and opaque cover 101 permit ventilation of the infusate conducted through channels 126.

The coring atherectomy probe and system of the present invention may also find advantageous applications in regions of the body outside the prostate and for indications other than amelioration of BPH. For example, the mechanical cutters of the coring probe may be useful in an array of orthopedic procedures for such tasks as tissue shaving, debridement, and bone resurfacing. Live aspiration can be useful to immediately suction out particulate bone fragments as bone is cut. The types of orthopedic procedures in which the probe can be used include but are not limited to: hip replacements, knee surgeries, shoulder surgeries, etc. In its broadest sense the invention is intended to cover the probe as adapted and applied for such orthopedic purposes and all other uses.

From the above description of the invention, those skilled in the art will perceive improvements, changes and modifications. Such improvements, changes and modifications within the skill of the art are regarded as covered by the appended claims directly or as equivalents.

What is claimed is:

1. A probe of configured for transperineal insertion into a prostate for mechanically cutting comprising:
    a cutting core disposed in a housing, the cutting core having at least one sharp curved edge located in a distal region of the cutting core for cutting, the cutting core also having a channel formed therein for providing aspiration of fluid and bodily material while the sharp curved edge is cutting;
    the housing disposed around the cutting core, the housing having one or more openings or portals in a distal region thereof, at least one opening or portal being at least partially open at all times during the aspiration of fluid and bodily material;
    a transparent sheath disposed around the housing, the sheath having a plurality of grooves therein;
    a handpiece on an outside of a proximal end of the probe, the handpiece disposed around and receiving the cutting core and the housing; and
    a cone having a truncated cone configuration disposed inside a distal region of the handpiece within an inner surface of the handpiece, wherein the aspiration channel of the cutting core, the housing, and the sheath are received by and extend distally from the cone, the cone having a chamber therein for supplying the plurality of grooves in the sheath with fluid.

2. The probe of claim 1, further comprising:
    an aspiration pipe, defined as a proximal portion of the cutting core within the handpiece, the aspiration pipe received by and extending proximally from the cone; and
    a piston disposed around the aspiration pipe and configured for driving the cutting core, a first end of the piston having a spring and a second end of the piston having a stroke stop, wherein the spring is configured for providing a return force and the stroke stop is configured for maintaining a space for air pressure to drive the piston.

3. The probe of claim 2, further comprising a pneumatic air supply pipe within the handpiece and terminating at the space maintained by the stroke stop for air pressure to drive the piston, the pneumatic air supply pipe configured to supply air to drive the piston.

4. The probe of claim 1, further comprising a plurality of pipes disposed within the handpiece, at least one of the plurality of pipes received by and extending proximally from the cone.

5. The probe of claim 4, the plurality of pipes including a visualization pipe, an infusion pipe, and an aspiration pipe;
    each of the visualization pipe, the infusion pipe, and the aspiration pipe being received by and extending proximally from the cone;
    wherein the infusion pipe is configured to deliver fluid to the chamber of the cone for supplying the plurality of grooves in the sheath with fluid.

6. The probe of claim 5, wherein the cutting core is a portion of the aspiration pipe distal to the cone.

7. The probe of claim 1, the cone having at least one indentation on a surface thereof configured to mate with a corresponding protrusion on an inner surface of the handpiece to hold the cone in position within the handpiece.

* * * * *